US012642986B2

(12) United States Patent
Eltorai et al.

(10) Patent No.: US 12,642,986 B2
(45) Date of Patent: Jun. 2, 2026

(54) ADHESIVE PHOTOTHERAPY METHOD, SYSTEM, AND DEVICES

(71) Applicant: Azulite, Inc., Marlborough, MA (US)

(72) Inventors: Adam E. M. Eltorai, Marlborough, MA (US); Lloyd Nelson, Largo, FL (US)

(73) Assignee: Azulite, Inc., Marlborough, MA (US)

( * ) Notice: Subject to any disclaimer, the term of this patent is extended or adjusted under 35 U.S.C. 154(b) by 11 days.

(21) Appl. No.: 18/120,212

(22) Filed: Mar. 10, 2023

(65) Prior Publication Data

US 2023/0277866 A1     Sep. 7, 2023

Related U.S. Application Data

(63) Continuation-in-part of application No. 17/360,029, filed on Jun. 28, 2021, which is a continuation-in-part of application No. 16/045,861, filed on Jul. 26, 2018, now Pat. No. 12,233,280.

(60) Provisional application No. 63/045,134, filed on Jun. 28, 2020.

(51) Int. Cl.
*A61N 5/00*          (2006.01)
*A61N 5/06*          (2006.01)

(52) U.S. Cl.
CPC .... *A61N 5/0616* (2013.01); *A61N 2005/0632* (2013.01); *A61N 2005/0645* (2013.01); *A61N 2005/0651* (2013.01)

(58) Field of Classification Search
CPC .... A61N 2005/0632; A61N 2005/0643; A61N 2005/0663; A61N 5/06
See application file for complete search history.

(56) References Cited

U.S. PATENT DOCUMENTS

| | | | |
|---|---|---|---|
| 5,549,660 A | 8/1996 | Mendes et al. | |
| 7,678,959 B2 | 3/2010 | Okada et al. | |
| 8,808,879 B2 | 8/2014 | Mochizuki et al. | |
| 9,415,237 B2 * | 8/2016 | Wagenaar Cacciola | ................... A61N 5/0616 |

(Continued)

FOREIGN PATENT DOCUMENTS

| | | | |
|---|---|---|---|
| WO | 2009081910 A1 | 7/2009 | |
| WO | 2010087559 A1 | 8/2010 | |
| WO | WO-2018226057 A1 * | 12/2018 | ........... A61L 2/0047 |

OTHER PUBLICATIONS

International Search Report, PCT/US2023/018275, Nov. 29, 2023, pp. 1-5.

*Primary Examiner* — Sana Sahand
(74) *Attorney, Agent, or Firm* — Armis IP Law, LLC

(57) ABSTRACT

A dermatological phototherapy device, system, and method, including a light emitting device configured and arranged to emit light from a bottom surface thereof; and an attachment portion having an aperture therethrough configured to permit light through. The attachment portion is configured to retain the device to a user's skin using a circumferential silicone skirt and bathe the skin with phototherapeutic light from the light emitter. Attachment of the device may be preceded with the application of synergistic fluid, ointment, gel, cream, lotion, foam, soap, or other solutions which may or may not consist of known topical treatment agents, augment device attachment to the skin, and/or have photodynamic properties. The light emitted may be any wavelength, combinations of wavelengths, intensity, pulse frequency, and exposure duration.

15 Claims, 24 Drawing Sheets

(56) References Cited

U.S. PATENT DOCUMENTS

| | | | |
|---|---|---|---|
| 2003/0029456 A1 | 2/2003 | Lambert | |
| 2006/0173514 A1* | 8/2006 | Biel | A61K 9/703 |
| | | | 607/88 |
| 2008/0311178 A1 | 12/2008 | Ishikura et al. | |
| 2009/0043294 A1 | 2/2009 | Island et al. | |
| 2009/0254155 A1* | 10/2009 | Kanarsky | A61N 5/0613 |
| | | | 607/2 |
| 2012/0225110 A1 | 9/2012 | Hashino et al. | |
| 2012/0289885 A1 | 11/2012 | Cottrell et al. | |
| 2013/0144364 A1* | 6/2013 | Wagenaar Cacciola | |
| | | | A61N 5/0625 |
| | | | 607/90 |
| 2014/0379050 A1* | 12/2014 | Pai | A61N 5/0619 |
| | | | 607/88 |
| 2016/0361564 A1 | 12/2016 | Pai et al. | |
| 2018/0015297 A1 | 1/2018 | Kahn | |
| 2020/0178848 A1 | 6/2020 | Hyde et al. | |
| 2020/0261738 A1* | 8/2020 | Macgilp | A61N 5/0616 |
| 2021/0393975 A1 | 12/2021 | Eltorai et al. | |

* cited by examiner

234

222

218

220

216

214

236

226

212

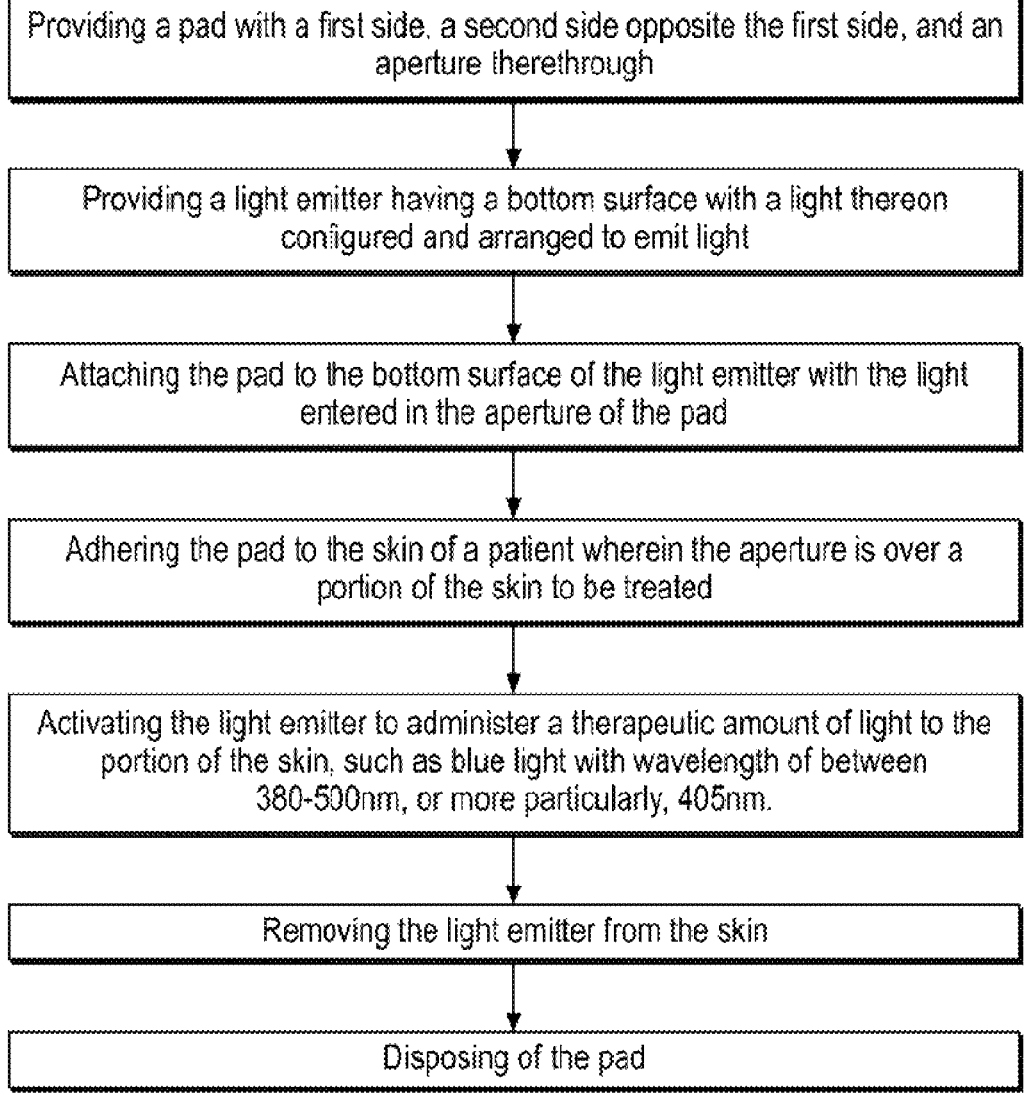

Providing a pad with a first side, a second side opposite the first side, and an aperture therethrough Providing a light emitter having a bottom surface with a light thereon configured and arranged to emit light Attaching the pad to the bottom surface of the light emitter with the light entered in the aperture of the pad Adhering the pad to the skin of a patient wherein the aperture is over a portion of the skin to be treated Activating the light emitter to administer a therapeutic amount of light to the portion of the skin, such as blue light with wavelength of between 380-500nm, or more particularly, 405nm.

Removing the light emitter from the skin

Disposing of the pad

ADHESIVE PHOTOTHERAPY METHOD, SYSTEM, AND DEVICES

RELATED APPLICATIONS

This patent application is a continuation-in-part (CIP) under 35 U.S.C. § 120 of U.S. patent application Ser. No. 17/360,029, filed Jun. 28, 2021, entitled "ADHESIVE PHOTOTHERAPY METHOD, SYSTEM, AND DEVICES," which is a continuation-in-part (CIP) under 35 U.S.C. § 120 of U.S. patent application Ser. No. 16/045,861, filed Jul. 26, 2018, entitled "ADHESIVE PHOTOTHERAPY METHOD, SYSTEM, AND DEVICES FOR ACNE," and claims the benefit under 35 U.S.C. § 119(e) of U.S. Provisional Patent App. No. 63/045,134, filed Jun. 28, 2020, entitled "IMPROVED ADHESIVE PHOTOTHERAPY METHOD, SYSTEM, AND DEVICES," incorporated herein by reference in entirety.

FIELD OF THE INVENTION

The present patent document relates generally to methods for treating acne, and more particularly to a phototherapy device, system, and method of treating of acne and acne scars.

BACKGROUND OF THE INVENTION

Acne, also known as acne vulgaris is a common cutaneous disorder which can affect adolescents and young adults alike. Acne is a long-term skin disease that occurs when hair follicles are clogged with dead skin cells and oil from the skin. It is characterized by blackheads or whiteheads, pimples, oily skin, and possible scarring. It primarily affects areas of the skin with a relatively high number of oil glands, including the face, upper part of the chest, and back. The resulting appearance can lead to anxiety, reduced self-esteem and, in extreme cases, depression or thoughts of suicide. Patients that suffer from this condition can additionally experience significant scaring of the skin which can result in psychological side effects. Thus, there has been much research into prevention of acne vulgaris and reduction of the resulting scaring. In 2015, acne was estimated to affect 633 million people globally, making it the 8th most common disease worldwide. Acne commonly occurs in adolescence and affects an estimated 80-90% of teenagers in the Western world. Children and adults may also be affected before and after puberty. Although acne becomes less common in adulthood, it persists in nearly half of affected people into their twenties and thirties and a smaller group continue to have difficulties into their forties. Typical features of acne include increased secretion of oily sebum by the skin, microcomedones, comedones, papules, nodules (large papules), pustules, and often results in scarring. The appearance of acne varies with skin color. It may result in psychological and social problems.

Genetics is thought to be the primary cause of acne in 80% of cases. The role of diet and cigarette smoking is unclear, and neither cleanliness nor exposure to sunlight appear to play a part. During puberty, in both sexes, acne is often brought on by an increase in hormones such as testosterone. A frequent factor is excessive growth of the bacterium *Propionibacterium acnes*, which is normally present on the skin.

Many treatment options for acne are available, including lifestyle changes, medications, and medical procedures. Eating fewer simple carbohydrates such as sugar may help.

Topical treatments applied directly to the affected skin, such as azelaic acid, benzoyl peroxide, salicylic acid, tretinoin, adapalene, tazarotene, isotretinoin, clindamycin, erythromycin, dapsone, topical combination products (benzoyl peroxide and clindamycin; benzoyl peroxide and erythromycin; clindamycin and tretinoin; benzoyl peroxide and adapalene), are commonly used. Antibiotics and retinoids are available in formulations that are applied to the skin and taken by mouth for the treatment of acne. However, resistance to antibiotics may develop as a result of antibiotic therapy. Acne is additionally treated with topical creams and cleansers, in addition to the aforementioned prescription antibiotics, anti-inflammatory medications, and vitamin A derivatives, which can have harmful side effects or adverse reactions. Several types of birth control pills help against acne in women. Isotretinoin pills are usually reserved for severe acne due to greater potential side effects. Early and aggressive treatment of acne is advocated by some in the medical community to decrease the overall long-term impact to individuals.

Acne scars are caused by inflammation within the dermal layer of skin and are estimated to affect 95% of people with acne vulgaris. The scar is created by abnormal healing following this dermal inflammation. Scarring is most likely to take place with severe acne but may occur with any form of acne vulgaris. Acne scars are classified based on whether the abnormal healing response following dermal inflammation leads to excess collagen deposition or loss at the site of the acne lesion. Atrophic acne scars have lost collagen from the healing response and are the most common type of acne scar (account for approximately 75% of all acne scars). They may be further classified as ice-pick scars, boxcar scars, and rolling scars. Ice-pick scars are narrow (less than 2 mm across), deep scars that extend into the dermis. Boxcar scars are round or ovoid indented scars with sharp borders and vary in size from 1.5-4 mm across. Rolling scars are wider than icepick and boxcar scars (4-5 mm across) and have a wave-like pattern of depth in the skin. The scars may also cause psychological and social problems.

Phototherapy using non-ultraviolet light has been shown to be effective at treating acne. While ultraviolet (UV) light has carcinogenic effects when exposed to the skin, non-UV light has been shown to be non-carcinogenic. Certain non-UV light wavelengths (such as visible light spectrum) possess antimicrobial effects, which are demonstrated to kill the bacteria causing acne. Some examples of light-based therapies include: broad-spectrum continuous-wave visible light sources (blue light, red light); intense pulsed light; laser sources including the potassium titanyl phosphate (KTP) laser, pulsed dye laser (PDL), and infrared lasers, photodynamic therapy; and photopneumatic technology. Clinician-administered light sources can be complex systems which require extensive training to use. At home light base therapies can be safe, effective, and can result in minimal complications when used according to the manufacturer's instructions. However, such at home light therapies can suffer from several deficiencies including the need for the user to hold the device in place for the entirety of the light therapy, thereby limiting the user to the use of one free hand—at best.

Current acne phototherapy devices require the patient to actively hold the phototherapy apparatus in place for the entirety of the light therapy session, thereby limiting the user to one free hand to perform any other activities. Other over the counter acne phototherapy devices can require a user sit in front of a stand mounted device which can preclude engagement in other activities. Such prior art devices affect the patient's ability to continue their normal activities of daily living, by tying up the user's hands or requiring the patient to sit still during treatment.

In another method of treatment, a full-face phototherapy mask may be used. Full face masks can enable hands-free phototherapy without the need for a user to sit at a stand. However, a mask has the disadvantage of being difficult to see out of during user and is only usable on the face. The user's impaired vision affects the user's ability to continue their normal activities of daily living.

A further configuration employs a perimeter skirt or flange of silicone or similar deformable material for affixation and firm contact with a patient's epidermal surface while irradiated by therapeutic light. The silicone flange tapers downward around the perimeter of the housing and engages a hydrocolloid patch, or alternatively a cream or gel, with adhesive properties for ensuring the deice remains affixed in a vertical position. The circumferential skirt surrounds the circular, elliptical or rounded edges of the housing slightly biased towards the skin surface for ensuring full skin contact around the periphery aided by adhesion of the housing from the transparent and adhesive hydrocolloid patch or gel.

Each of the issues above affects a patient's adherence to the clinical recommendation. Poor adherence reduces the efficacy of the therapeutic device. To improve adherence and, in turn, efficacy, the above issues need to be overcome. An improved device needs to require minimal behavioral change for the user and needs to allow the user to continue in their regular activities; an improved device should not occupy their hands, require them to be seated for prolonged periods of time in one place, nor obstruct their vision. Such requirements are particularly important given the demographic most commonly affected by acne—young, active teenagers and adults—who are generally on the move.

SUMMARY OF THE INVENTION

The phototherapy devices, systems, and methods disclosed herein solve the problems of the prior art by providing a phototherapy device that does not require a user to hold the device, sit in front of the device, or obstruct the user's vision. The devices do not require active engagement from the user during use, and therefore the user can avoid behavioral changes that have traditionally reduced adherence and effectiveness. Additionally, the device may be used on any area of the body.

In a first embodiment, the phototherapy device can include a light emitter configured and arranged to emit light from a bottom surface thereof; and a suction cup having an aperture therethrough. The light emitter can be configured and arranged to emit light through the aperture of the suction cup. The suction cup can be an integral, or separate, feature of the housing of the device. The suction cup can be flexible to permit the device to attach to a variety of contoured skin surfaces. Device attachment may be enhanced through the application of a fluid, ointment, gel, cream, lotion, foam, soap, or other solution. The fluid, ointment, gel, cream, lotion, foam, soap, or other solution may include known topical acne treatment, such as azelaic acid, benzoyl peroxide, salicylic acid, tretinoin, adapalene, tazarotene, isotretinoin, clindamycin, erythromycin, dapsone, topical combination products (benzoyl peroxide and clindamycin; benzoyl peroxide and erythromycin; clindamycin and tretinoin; benzoyl peroxide and adapalene). The light emitted may be varied for any wavelength or wavelength combinations of any intensities, pulse frequency, and exposure duration for phototherapeutic effects.

In an alternative embodiment, the phototherapy device can include a light emitter that is configured and arranged to emit light from a bottom surface thereof; and a pad having a first side with adhesive thereon, a second side opposite the first side, and an aperture therethrough. The pad can be connected to the bottom surface of the light emitter. The light emitter can be configured and arranged to emit light through the aperture of the pad. An optional case may hold the light emitter and a number of disposable pads as a kit.

In a further configuration, a transparent hydrocolloid patch is provided for providing an adhesive force, pus- and fluid-absorptive properties, combined with a medicinal substance for adhering the medicated patch directly to the afflicted area while maintaining a transparency for therapeutic light.

BRIEF DESCRIPTION OF THE DRAWINGS

These and other features, aspects, and advantages of the present invention will become better understood with reference to the following description, appended claims, and accompanying drawings where:

FIG. 11 is a flowchart of an exemplary method of using a phototherapy device to treat a skin disorder;

DESCRIPTION OF THE PREFERRED EMBODIMENT

As will be described in greater detail below, the phototherapy devices, system, and methods are described herein. The devices can generally include a light emitter and an attachment device with an aperture that attaches to the light emitter. The attachment device can permit the device and the associated housing to removably attach to a user's skin at a variety of locations without concern for where the device is going to be used. Further, the attachment device advantageously allows for application of light-based phototherapy without the need for the user to continuously hold the device in place. Further still, the small foot print of the device advantageously will not obstruct the user's ability to see or perform other daily activities.

Figure 1A:
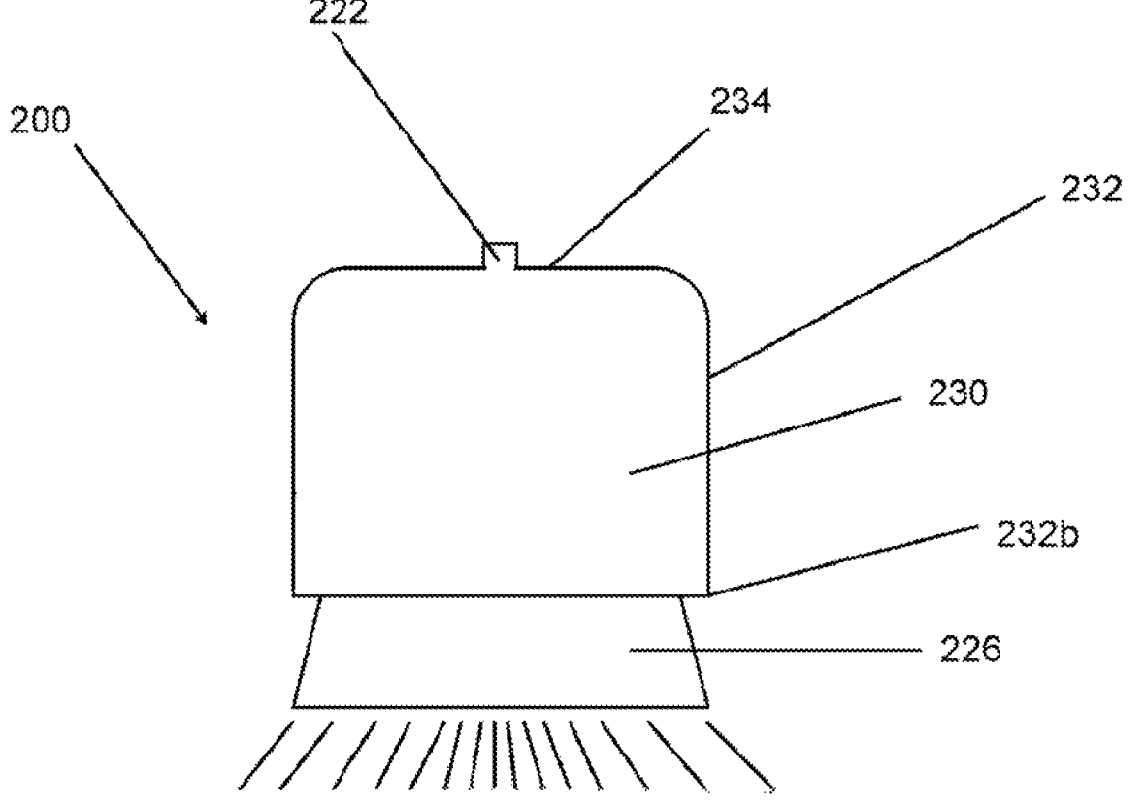
FIG. 1A is a side schematic view of a first exemplary embodiment of a phototherapy device.
Figure 1B:
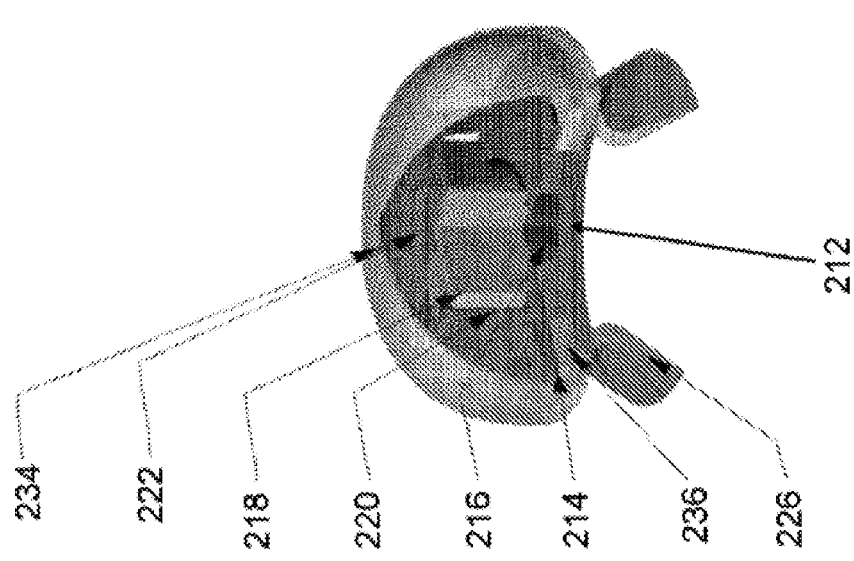
FIG. 1B is a partial cutaway perspective view of the device of FIG. 1A.

In a first embodiment, referring now to FIGS. 1A and 1B, a phototherapy device is shown generally at 200. The device can generally include a housing 230 and a light emitter 212. The housing 230 can be formed from materials including silicone, vinyl, rubber, and other materials including those having natural antimicrobial properties, or impregnated with antimicrobial materials. As shown, the housing 230 can generally include an upper most surface 234, a body portion 232, and a suction portion 226. The upper most surface 234 can have a protruding button 222 or can be flexible so that a user can interface with a button disposed therein. The button 222 can be used to operate the light emitter 212 as will be discussed further below. The housing 230 can be in the form of a dome like shell which can generally house the light emitter 212, a battery 218, and a programable circuit board 214. In some embodiments, a stiffener 236 can support the programable circuit board 214 within the housing 230. Depending downward from the lower end of the body 232b, a suction portion, or cup, 226 can extend. The suction cup 226 can include an aperture therethrough to permit light from the light emitter 212 to shine therethrough. The suction portion 226 can be compressible so that upon compression of the suction cup 226, air is evacuated, and a vacuum is created to retain the device 200 to the skin. In use, at the same time as the vacuum seal is created, the button 222 can be actuated in a single press to secure the device 200 to the skin and to activate the light emitter 212. Alternatively, the button 222 can be actuated separately from attaching the device 200 to the skin. In some use cases, it may be beneficial to apply a fluid, ointment, gel, cream, lotion, foam, soap, or other solution, to the skin before attachment of the device 200. In such a case, the suction cup 226 may have improved suction, and adhesion, to the skin. The fluid, ointment, gel, cream, lotion, foam, soap, or other solution can be azelaic acid, benzoyl peroxide, salicylic acid, tretinoin, adapalene, tazarotene, isotretinoin, clindamycin, erythromycin, dapsone, topical combination products (benzoyl peroxide and clindamycin; benzoyl peroxide and erythromycin; clindamycin and tretinoin; benzoyl peroxide and adapalene), each of which are medications used to treat mild to moderate acne. In some embodiments, medications used to treat mild to moderate acne can be enhanced by the phototherapy light device. Alternatively, the fluid, ointment, gel, cream, lotion, foam, soap, or other solution can be any of a composition and consistency which can have synergistic effects with the light. The fluid, ointment, gel, cream, lotion, foam, soap, or other solution can be provided in a tube, jar, or any other type of container. In some exemplary embodiments, the device 200 can be packaged with one or more containers of the fluid, ointment, gel, cream, lotion, foam, soap, or other solution. For example, a tube of synergistic fluid, ointment, gel, cream, lotion, foam, soap, or other solution can be provided in a single package with at least one device 200. In some examples, the package can include a plurality of tubes of synergistic fluid, ointment, gel, cream, lotion, foam, soap, or other solution, either the same kinds or different types, and a plurality of devices 200.

Figure 3:
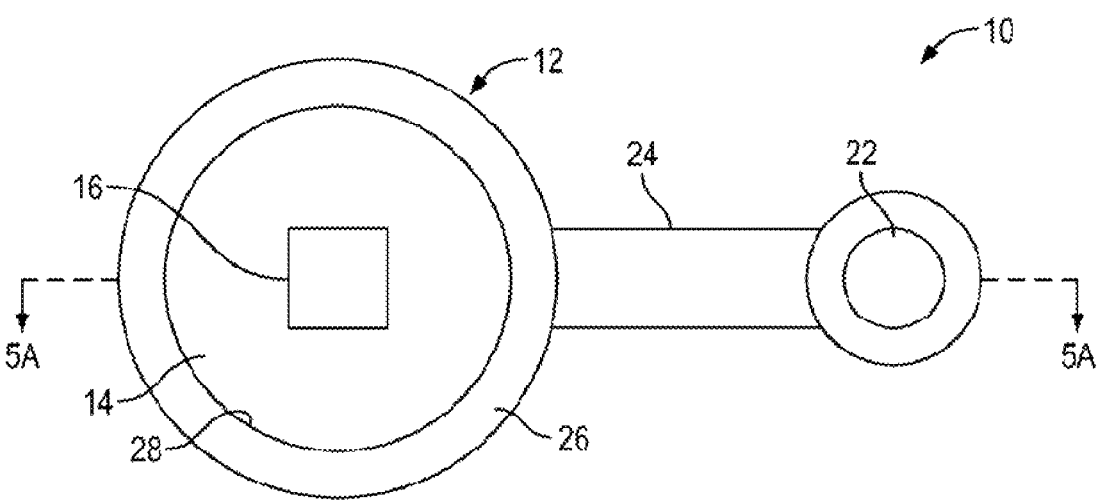
FIG. 3 is a bottom view of an alternative exemplary embodiment of a phototherapy device with a cover removed and a switch in an unfolded position.
Figure 4:
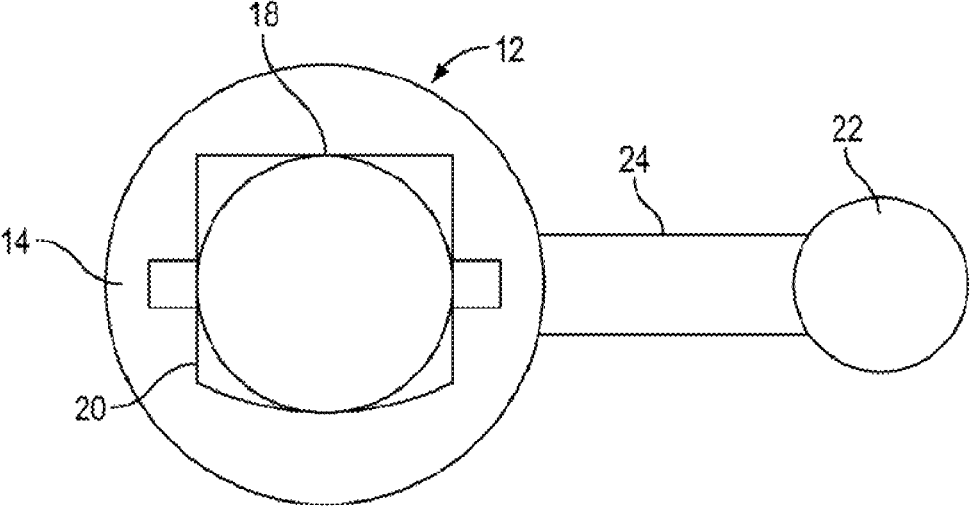
FIG. 4 is a top view of an exemplary embodiment of a phototherapy device with the cover removed and a switch in an unfolded position.

As noted above, the device 200 can generally include a light emitter 212 having a circuit board 214 with a light emitting diode ("LED") 216 on a bottom surface thereof. In a first embodiment, the LED 216 is a blue-light LED. Alternatively, the LED 216 can be a red-light LED, or a combination thereof. Further still, the LED 216 can be any type of light source which produces a therapeutic benefit. A battery 218 can be retained in a battery cage 220 on a top surface of the circuit board 214. The switch 222, such as a momentary switch, can be connected to the circuit board 214 with ribbon cable (not shown). A circuit can be formed with the LED 216, switch 222 and battery 218. The circuit can be programmed to operate the LED 216 for a predetermined time when the switch 222 is depressed. The circuit can be substantially the same as the circuit shown in FIGS. 3 and 4.

Figure 2:
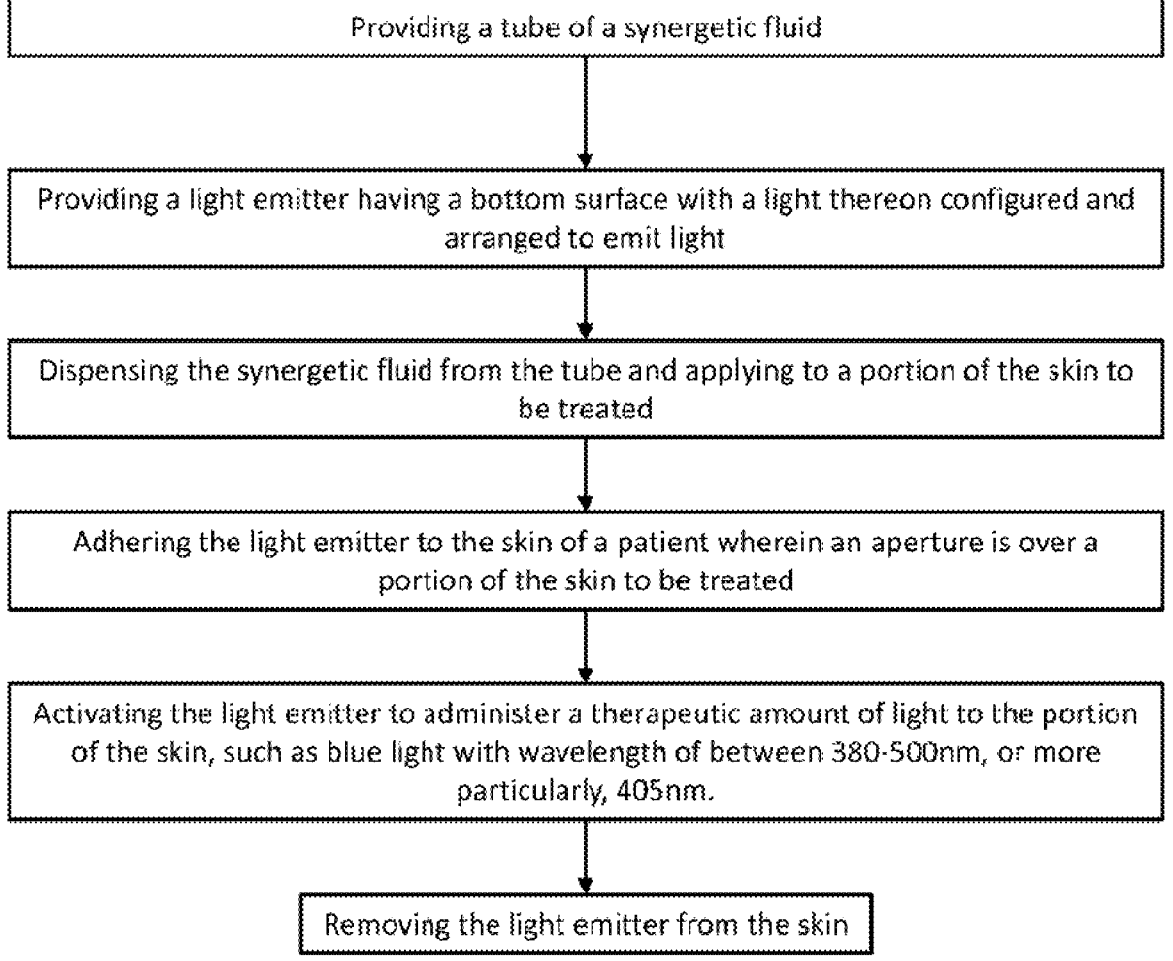
FIG. 2 is a flowchart of an exemplary method of using a phototherapy device of FIGS. 1A and 1B to treat a skin disorder.

In a first exemplary method of use, as shown in FIG. 2, the user is provided with a pre-application, synergistic fluid, ointment, gel, cream, lotion, foam, soap, or other solution and a light emitting device in first and second method steps. The user can dispense the synergetic fluid, ointment, gel, cream, lotion, foam, soap, or other solution from a tube in a third step and optionally apply a layer of the gel to the area of the skin to be treated by the device. In one example, the area can be over an area of acne on the face, back, chest, or any other location on the human body. Alternatively, the application of the gel can be omitted. After the application of the gel, in a fourth step, the device can be adhered or pressed onto the skin, in the area of the gel. Pressing of the device can create a vacuum seal by the suction cup on the skin, in the fourth step, and simultaneously, can actuate the button to activate the light source to bathe the skin in light, in the fifth step. Alternatively, the creation of the vacuum and the activation of the button can be performed separately. After a predetermined amount of time, the light source can be deactivated, either automatically, or by pressing the switch again. The user can then lift a lip of the suction cup to release the vacuum seal and thereby release the device from the skin, in the sixth step. The exemplary method can be performed at various stages of the acne progression. For example, the method can be performed upon the emergence of a lesion to reduce the severity of the acne by killing pathogenic bacteria; during an active breakout of acne to expedite recovery, reduce the inflammation, reduce erythema and bacteria, and improve the overall outcome; or after the acne has cleared up to reduce scar formation and severity to improve the healing. Moreover, a user can perform the method during one, two or all the stages.

Referring now to FIGS. 3-7C, an embodiment of the phototherapy device is shown generally at 10. The device 10 generally includes a light emitter 12 having a circuit board 14 with a light emitting diode ("LED") 16 on a bottom surface thereof. A battery 18 is retained in a battery cage 20 on a top surface of the circuit board 14. A switch 22, such as a momentary switch is connected to the circuit board 14 with ribbon cable 24. A circuit is formed with the LED 16, switch 22 and battery 18 and is programmed to operate the LED 16 for a predetermined time when the switch 22 is depressed. A pad 26 is removably secured to the bottom surface of the circuit board 14. The pad 26 includes an inner surface 28 defining an aperture 30 for the LED 16.

Figure 5A:
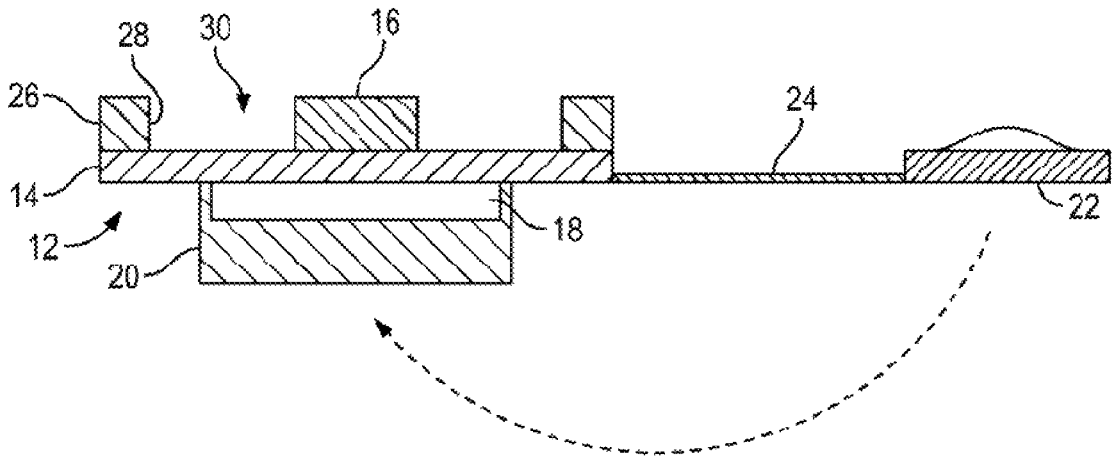
FIG. 5A is a cross-section view through line 5A-5A of FIG. 3, illustrating an exemplary embodiment of a phototherapy device with a switch in an unfolded position with the cover removed.
Figure 5B:
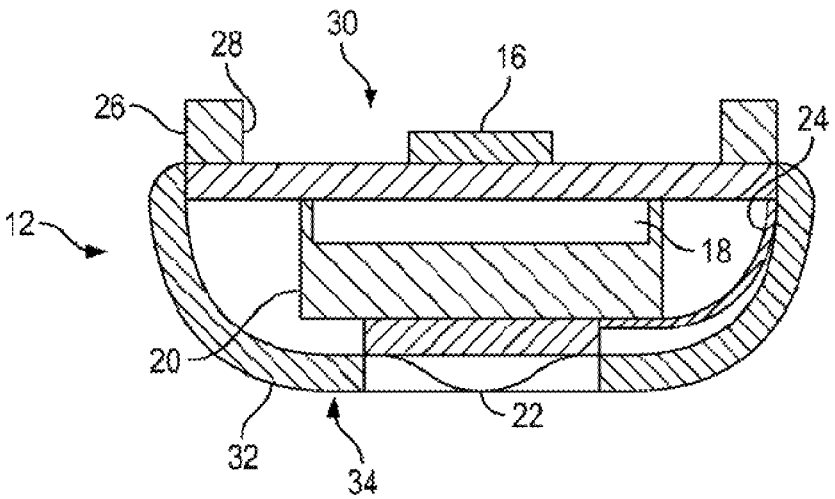
FIG. 5B is a side cross-section view illustrating an exemplary embodiment of a phototherapy device with a switch repositioned over a battery cage thereof and cover enclosing the device.
Figures 6A, 6B, 6C:
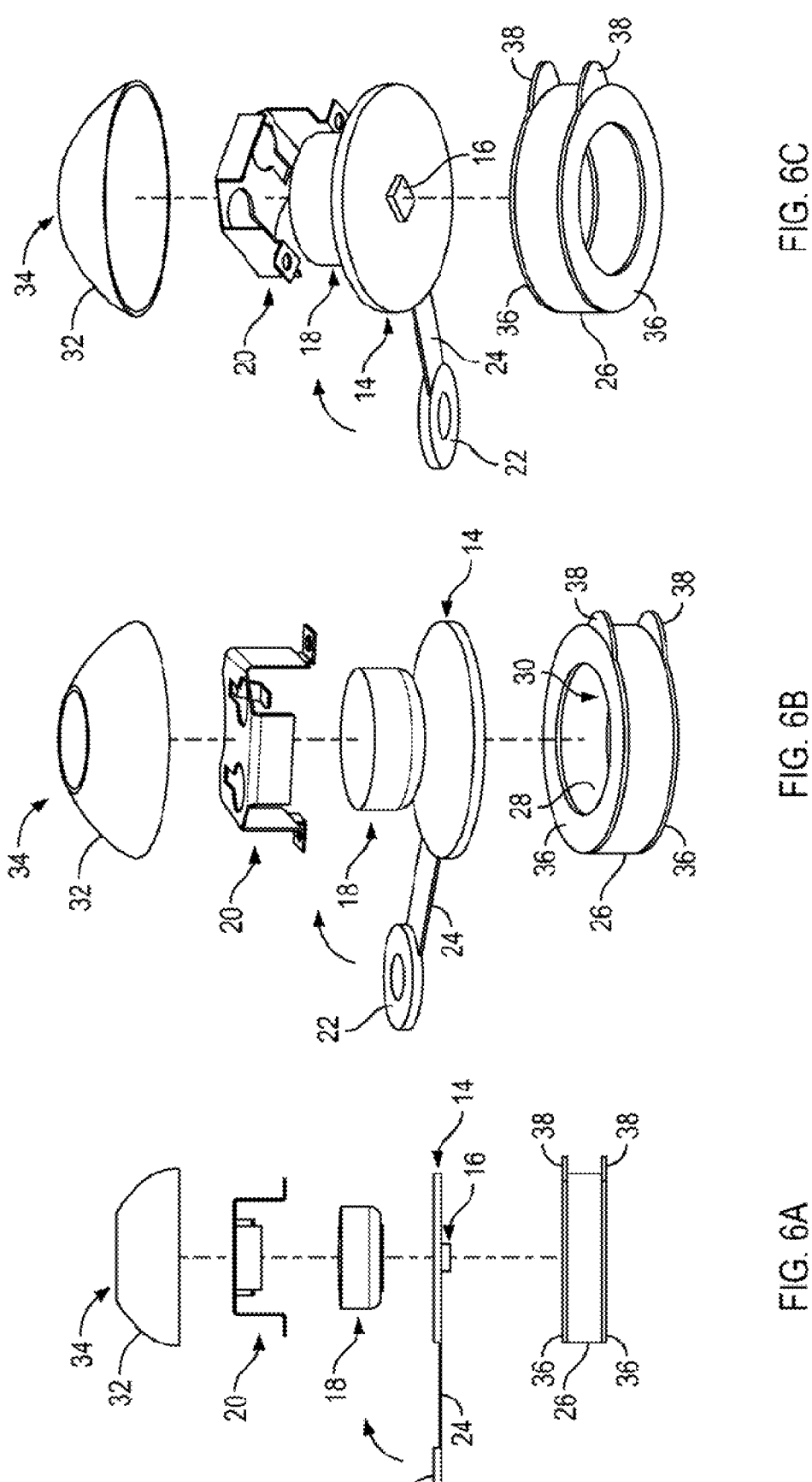
FIG. 6A is an exploded elevation view of an exemplary embodiment of a phototherapy device.
FIG. 6B is an exploded top view of an exemplary embodiment of a phototherapy device.
FIG. 6C is an exploded bottom view of an exemplary embodiment of a phototherapy device.
Figure 7A:
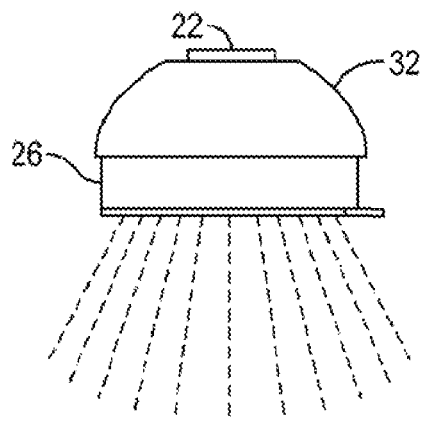
FIG. 7A is a side elevation view of an exemplary embodiment of a phototherapy device.
Figure 7B:
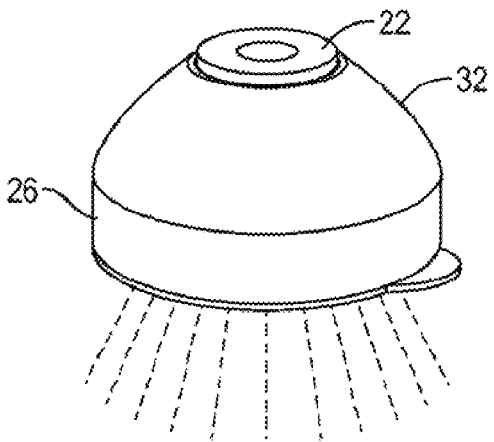
FIG. 7B is a top perspective view of an exemplary embodiment of a phototherapy device.
Figure 7C:
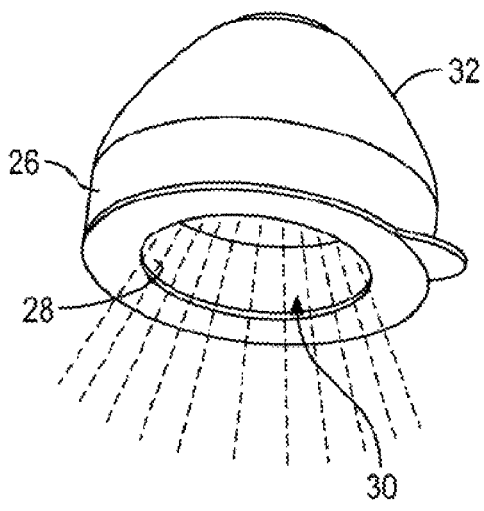
FIG. 7C is a bottom perspective view of an exemplary embodiment of a phototherapy device.

Referring to FIGS. 5A and 5B, the switch 22 is folded over the battery cage 20. Best seen in FIGS. 7A-7C, a cover 32 encloses the top surface of the circuit board 14, batter 18 and battery cage 22, leaving only the switch 22 exposed through an aperture 34 in the cover 32. The cover 32 may attach to the circuit board 14 via a snap-fit, twist-fit, threads and/or fasteners.

In one embodiment, the pad 26 may be ring-shaped; however, the pad 26 may have a different shape. Similarly, the aperture 30 in the pad 26 may be circular or have another profile. The profile of the aperture 30 need not be the same as the profile of the outer shape of the pad 30. For instance, the pad 26 may have a circular profile while the aperture 30 has a square profile. The pad 26 may be formed from a foam material having a thickness sufficient to elevate the circuit board 14 and LED 16 away from a person's skin. The pad 26 may include adhesive with a peelable, protective layer 36 on a top side and/or a bottom side of the pad (best seen in FIGS. 6A-6C). The protective layer may include a tab 38 to assist with removal of the protective layer 36 from the adhesive of the pad 26. The adhesive is preferably a weak adhesive, allowing the pad 26 to be removed from the device 10 and/or skin of the person without tearing of the pad 26, damage to the device 10, or discomfort to the person. The top surface of the pad 26 may be adhered to the device 10 and the bottom surface of the pad 26 adhered to the skin of the person.

Figure 8A:
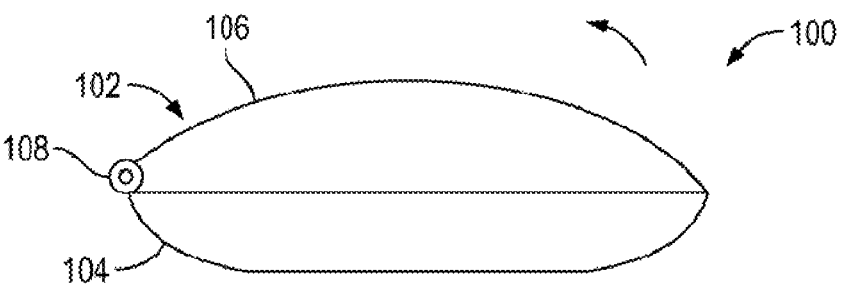
FIG. 8A is a side elevation view of an exemplary embodiment of a kit for a phototherapy device with a lid in a closed position.
Figure 8B:
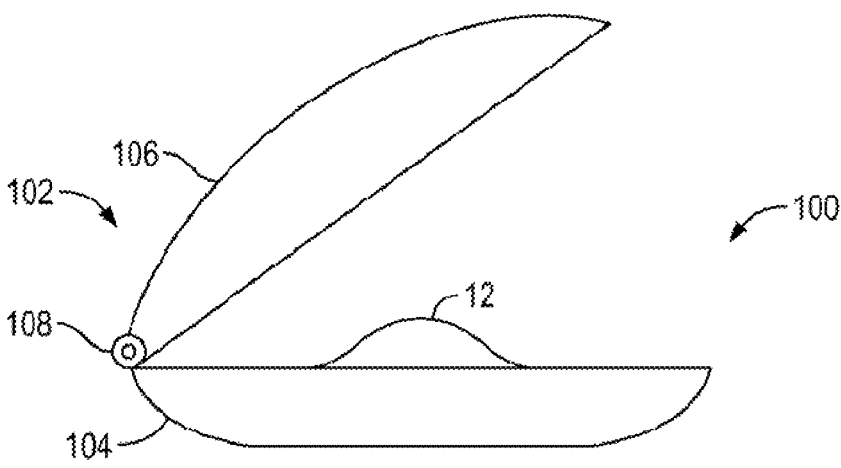
FIG. 8B is a side elevation view of an exemplary embodiment of a kit for a phototherapy device with a lid in an open position.
Figure 9:
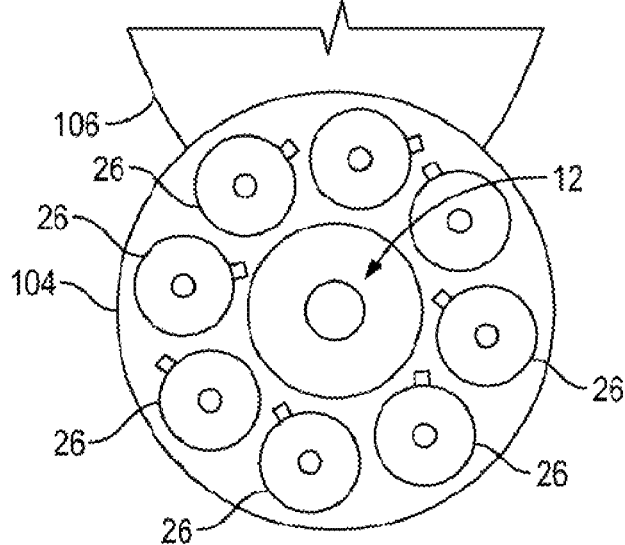
FIG. 9 is a partial top view of an exemplary embodiment of a kit for a phototherapy device with a lid in an open position.

Referring to FIGS. 8A, 8B and 9, an exemplary embodiment of a kit for a phototherapy device is shown generally at 100. The kit 100 may include a case 102 configured to hold a phototherapy device 10 having a light emitter 12 and a number of disposable pads 26.

In some embodiments, the case 102 may generally be in a clamshell configuration with a bottom portion 104 and a top portion 106 hinged to the bottom portion 104. The top portion 106 may pivotally open and close about the hinge 108. In one embodiment, the case 100 is circular, with a first location located in a center of the bottom portion 106 the case 100 to hold a light emitter 12 and a number of second locations located about the periphery of the bottom portion 106 of the case 100, configured to hold a number of disposable pads 26. Other case configurations may be used. The number of disposable pads 26 may be selected based on the number of treatments prescribed, such as 7-10, for example.

Depressing the switch 22 activates the LED 16 for a predetermine treatment period. For instance, a treatment period may be thirty minutes. After the treatment period lapses, the LED 16 is switched off. In addition, the light emitter 12 may deactivate after a specified total number of prescribed uses, such as 7-10 treatments. Optionally, the circuit board 14 may be further programmed to pulse, change the wavelength, or intensity of the emitted light from the LED 16 according to the prescribed treatment regimen.

The LED 16 may be configured to emit a non-UV light, such as blue light in wavelengths from 380 nm to 500 nm. In particular, blue light in wavelengths of about 405 nm may be used.

Figure 10A:
FIG. 10A is an illustration of a person applying an exemplary embodiment of a phototherapy device to their skin.
Figure 10B:
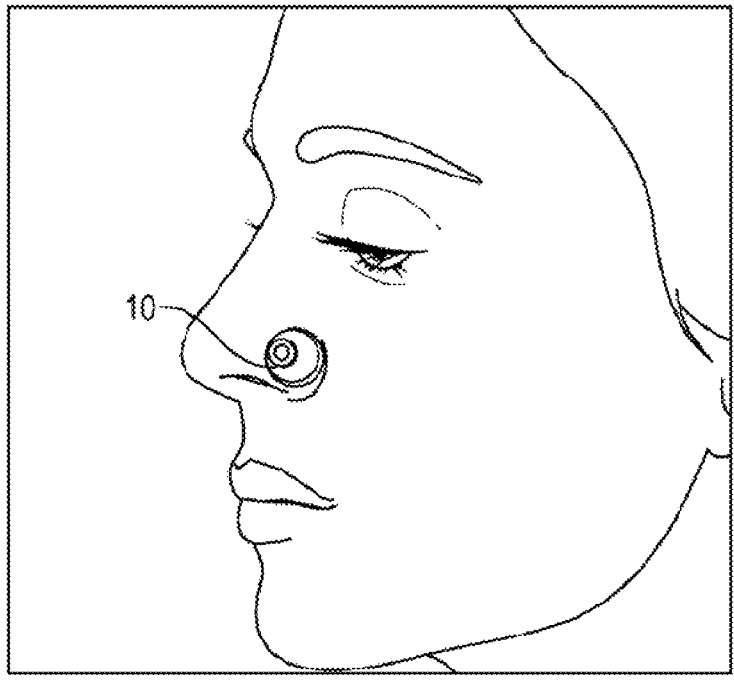
FIG. 10B is an illustration of a person with an exemplary embodiment of a phototherapy device applied to the skin.

Referring to FIGS. 10A, 10B and 11, a method of using the phototherapy device of FIGS. 3-9, to treat a skin disorder such as acne, is shown generally.

In a first and second steps, the user is provided a pad and light emitter as described above, which may be in a case of the kit described above. In a third step, the user opens the case and selects a pad. The user then peels away the protective layer from one side of the adhesive of the pad and attaches the pad to the light emitter. In particular, the user removes the might emitter from the case and press the exposed first layer of adhesive of the pad onto the bottom surface of the device, being careful to center the pad on the device.

In a fourth step, the user peels away a protective layer from the other, exposed side of the pad, exposing the second layer of adhesive, and the device is then applied to the affected area of the skin with gentle pressure by pressing the exposed adhesive of the pad against skin. For example, in FIG. 10A, a person is illustrated placing the phototherapy device on a portion of the skin near the user's nose.

In a sixth step, the user then activates the device by pressing the switch. After the predetermined time period lapses in a seventh step, the device shuts off and alerts the user. For example, in FIG. 10B, a person is illustrated wearing the phototherapy device during treatment.

In a seventh and eighth steps, the user then removes the device from the skin and peels the pad from the device and disposes the pad. The device is returned to the case until the next treatment. The foregoing method can be performed at various stages of the acne progression. For example, the method can be performed upon the emergence of a lesion to reduce the severity of the acne by killing pathogenic bacteria; during an active breakout of acne to expedite recovery, reduce the inflammation, reduce erythema and bacteria, and improve the overall outcome; or after the acne has cleared up to reduce scar formation and severity to improve the healing. Moreover, a user can perform the method during one, two or all the stages.

Therefore, it can be seen that the present invention provides a unique solution to the problem of treating a skin disorder, such as acne, with phototherapy that does not require that the person hold the device or sit still during treatment. Furthermore, the user may remain active and use both hands for other tasks.

As an alternative to the pressure-based suction cup approach disclosed above, an alternate configuration employs a lightweight device with a transparent hydrocolloid patch for securing a therapeutic light emitting device. FIGS. 12A-12F show various views of an epidermal, targeted treatment device defining the alternate configuration. Referring to FIGS. 12A-12F, an epidermal, targeted treatment device 200 includes a housing 201 having a top portion 210 and a bottom base 213. Finger recesses 215 provide either gripping regions and/or activation switches. The bottom base 213 includes a bottom window 221, or interface, formed of a transparent material, which may comprise all or a subset of the bottom base. A blue LED light source 231 and a red LED light source 233 emit therapeutic light through the bottom window, as discussed further below.

Figure 12A:
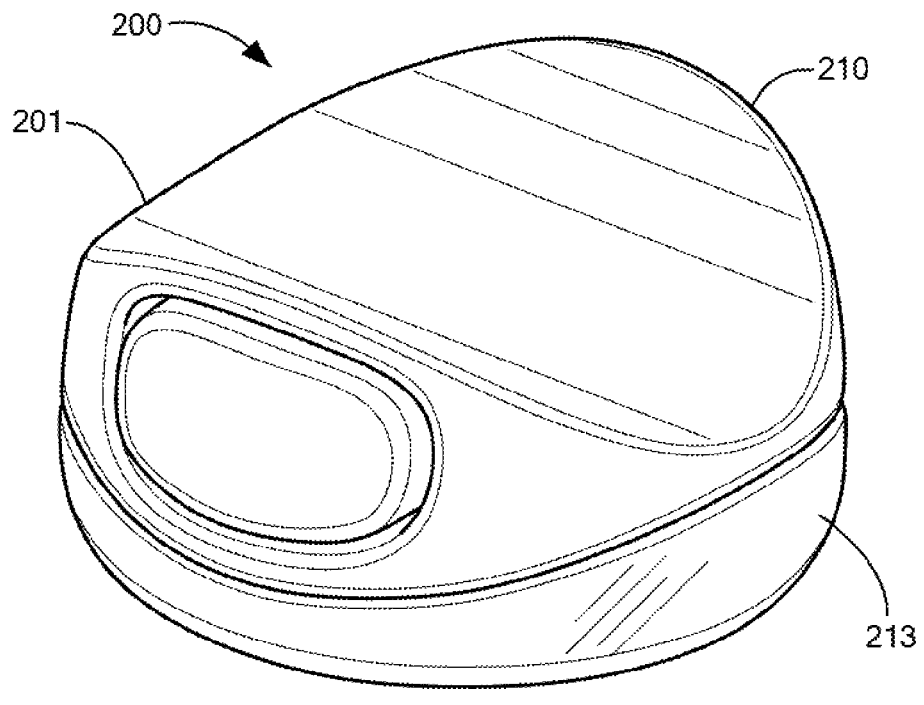
FIGS. 12A-12F show various views of an epidermal, targeted treatment device defining an alternate configuration, including a top perspective (FIG. 12A), side elevation (FIG. 12B), front elevation (FIG. 12C), Top view (FIG. 12D), bottom (FIG. 12E) and lower perspective (FIG. 12F)
Figure 12B:
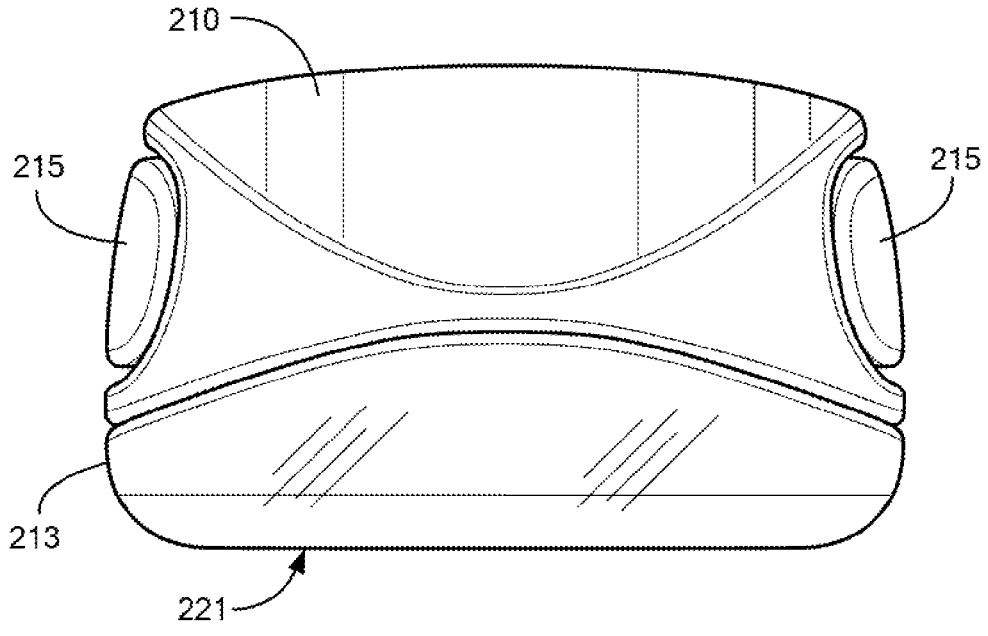
Figure 12C:
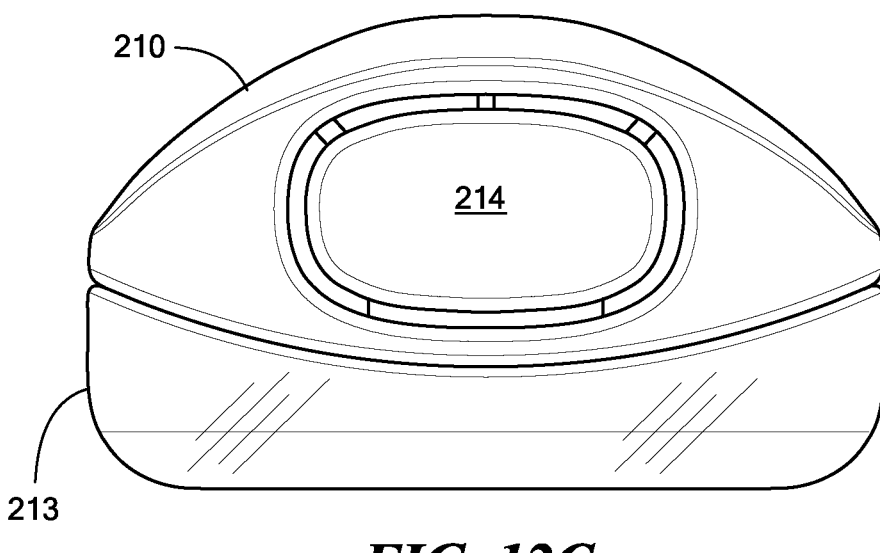
Figure 12D:
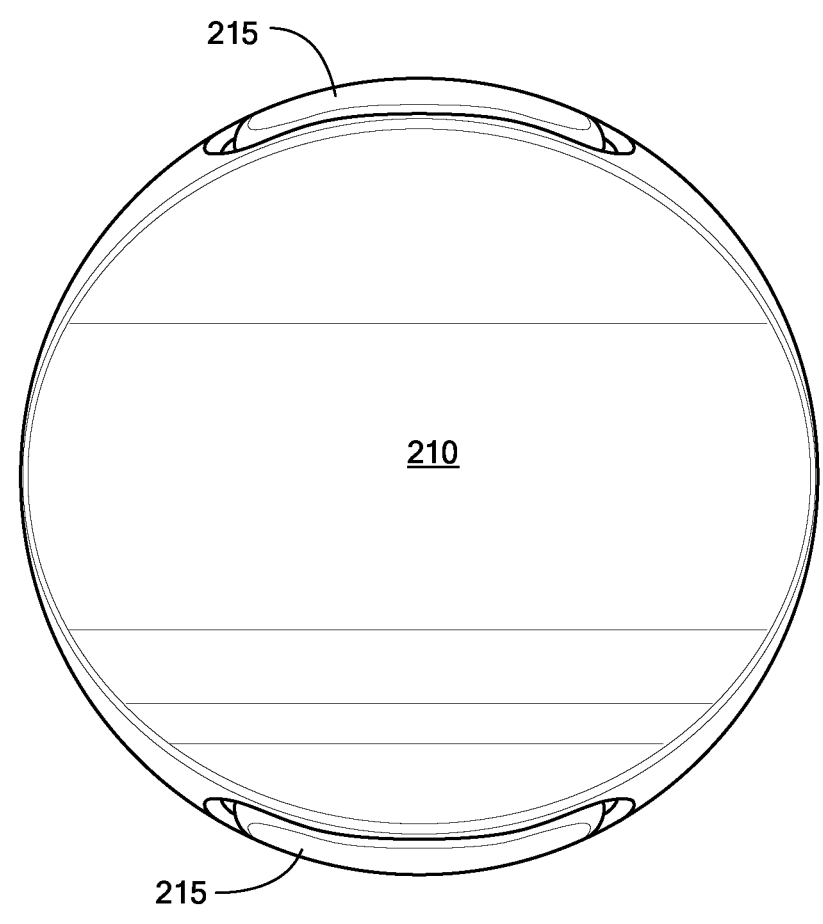
Figure 12E:
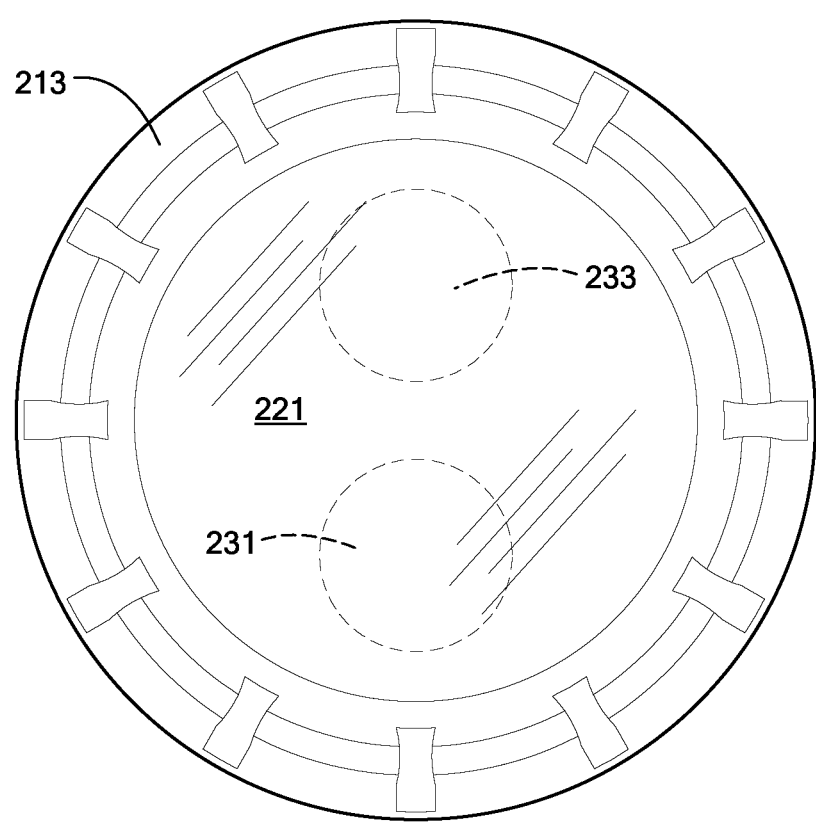
Figure 12F:
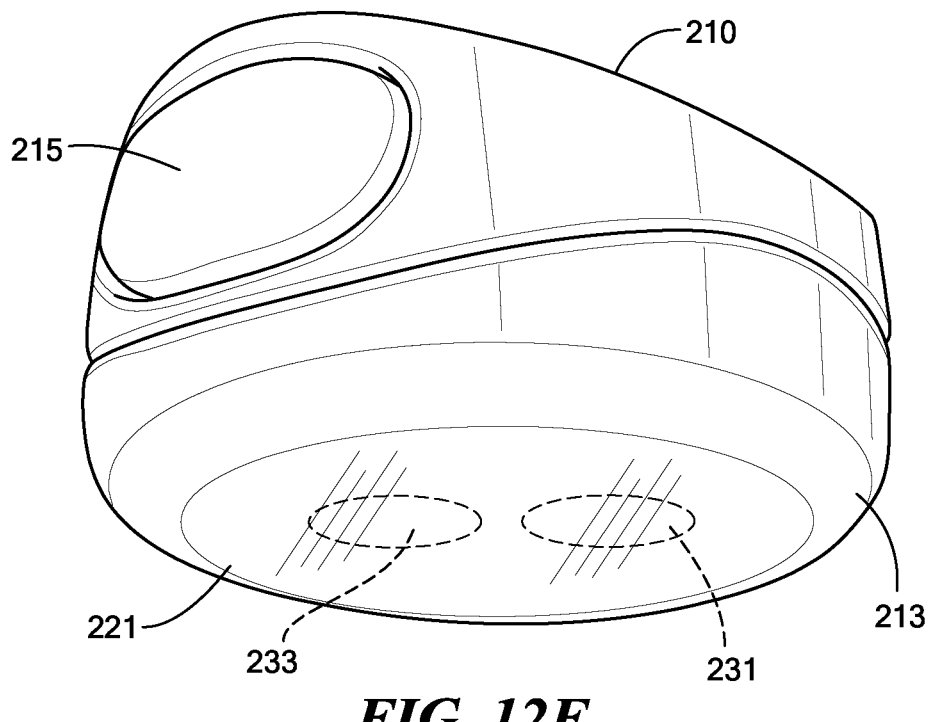
Figure 13:
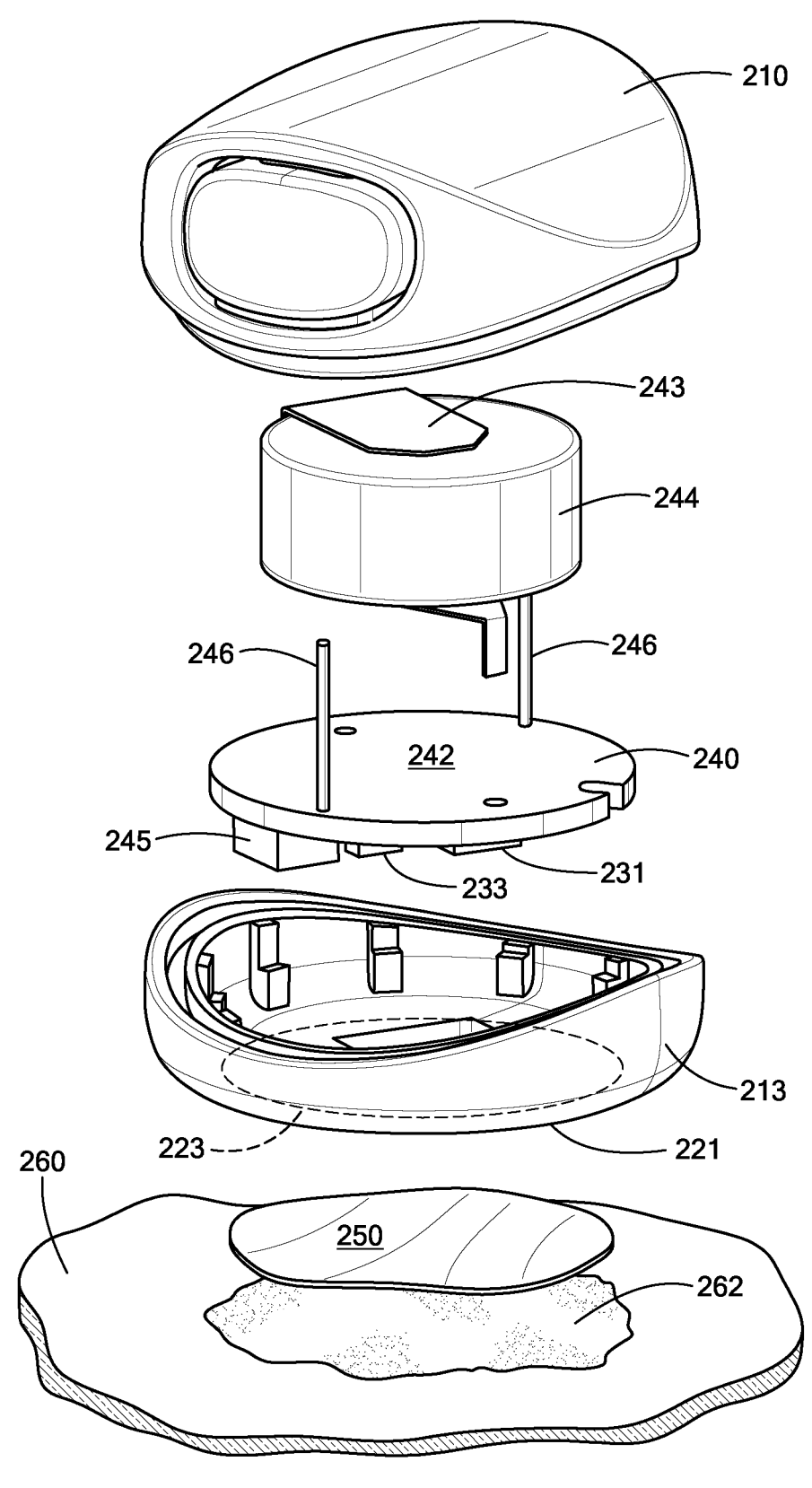
FIG. 13 is an exploded view of the device of FIGS. 12A-12F.

FIG. 13 is an exploded view of the device of FIGS. 12A-12F. Referring to FIGS. 12A-13, the housing 201 of the device 200 is adapted for dermal mounting on a patient for treatment of acne and other skin conditions mitigated by a combination of phototherapy and topical gels, creams or medication. The bottom window 221 is defined by a transparent material adapted for light passage and is receptive to an adhesive transparent hydrocolloid 223 for dermal fixation.

Secured inside the housing 201 are a circuit board 249, or PCB (Printed Circuit Board) with a circuit 242 including a light source (LEDs 231, 233), power supply or battery 244, and control logic 245 embedded in software or firmware on the circuit 242. The light source provided by the LEDs is directed downward at the bottom window 221 for passage of therapeutic light therethrough, such that the light source and control logic are configured to irradiate an afflicted region 262 on an dermal surface 260 at a predetermined wavelength of the therapeutic light.

The bottom window 221 is receptive to a transparent adhesive hydrocolloid. The transparent hydrocolloid is adhesive for retaining the housing and circuit disposed over a treatment site on an dermal surface of the patient. Both the bottom window 221 and the transparent adhesive hydrocolloid 223 have a transparency for permitting passage of the therapeutic light from the light source to the treatment site for imparting beneficial therapeutic effects, pus- and fluid-absorptive properties, and with impregnated topical agents 223.

In a particular configuration, the transparent adhesive hydrocolloid may be applied directly to the bottom window 221, an afflicted region 262, or in the form of a patch 250 disposed between the bottom window 221 and the dermal surface 260. The device 200, secured by the adhesive hydrocolloid patch, then remains fixed for a sufficient time for the light sources 231, 233 to have a beneficial effect. The transparent window 221 through which the therapeutic light is provided defines at least a portion of a bottom base 213, where the transparent window 221 is configured to pass the therapeutic light.

Figure 14:
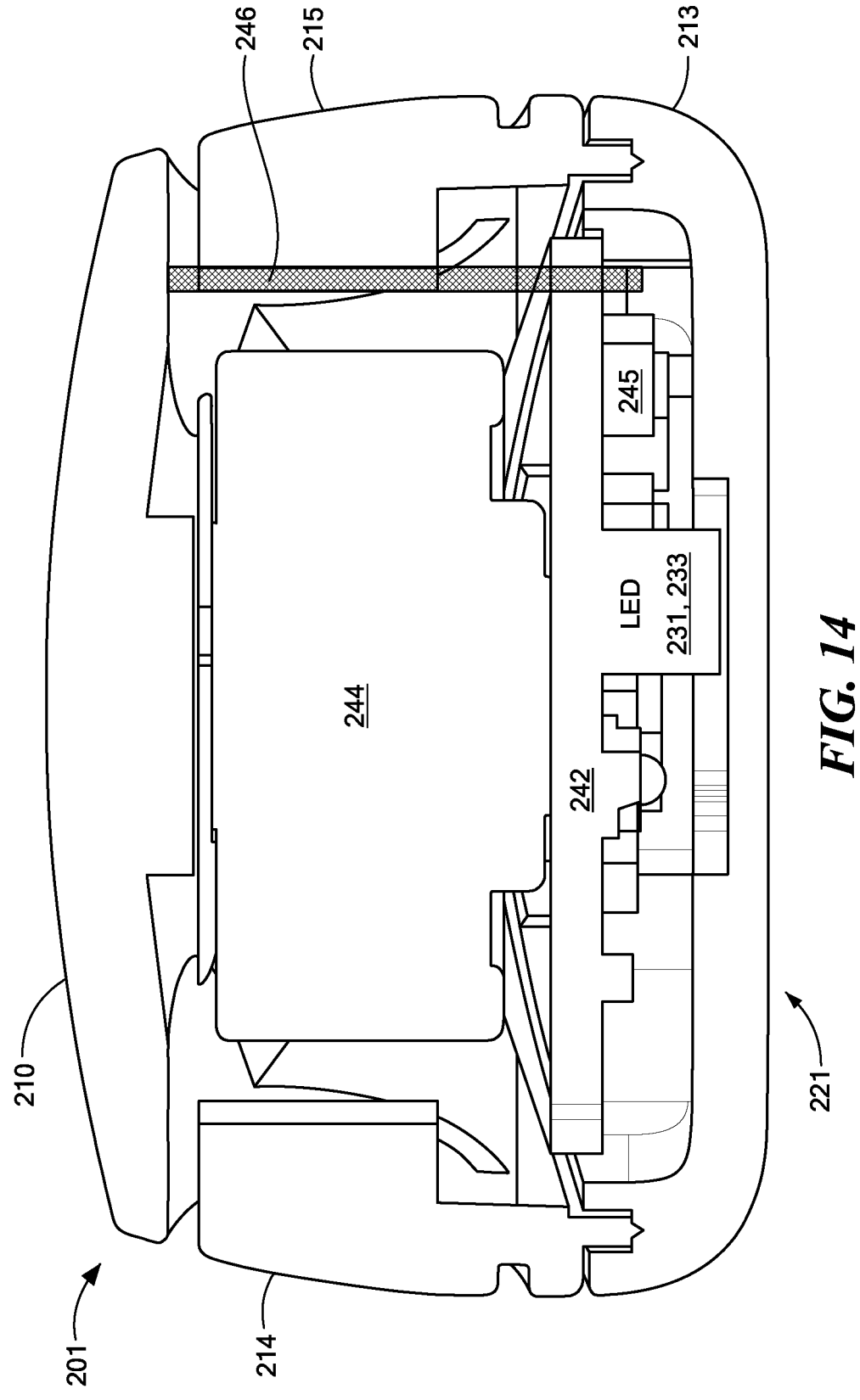
FIG. 14 is a side cutaway view of the device of FIG. 13.

FIG. 14 is a side cutaway view of the device of FIG. 13. Referring to FIGS. 12A-14, 10, the housing 201 includes the bottom base 213 and the top housing 210, such that the top housing defines a concave void for encapsulating the circuit 242, power supply 244 (battery) and the light source defined by one or more LEDs (Light Emitting Diodes) 231, 233. The bottom base 213 therefore supports the circuit board 242 encapsulating the control logic, in which the power supply is defined by the battery 244 attached to the circuit board 244 by battery contacts 246 on an opposed side of the circuit board 242 from the transparent window. A battery clip 243 further secures the battery 244 inside the enclosure. Upon activation or depression of the button 214, the battery contact 246 closes the circuit against the battery 244 for commencing the control logic to power and illuminate the LEDs 231, 233.

The circuit 242 includes one or more lighting elements based on the plurality of wavelengths and/or ranges employed for treatment, such that each of the lighting elements is configured for emitting a light having a corresponding wavelength, and each of the lighting elements is responsive to the control logic for emitting the light at a therapeutic sequence defining a predetermined duration and interval. In a particular configuration, the light may need only be activated for a brief interval, following a longer period of exposure to the medication and/or patch, or the device 200 may remain affixed to the dermal surface for a treatment duration.

The predetermined wavelength of the LEDs therefore includes a plurality of wavelengths, such that each wavelength of the plurality of wavelengths is selected based on a therapeutic result provided by the respective wavelength. In a particular configuration, therefore, a combination of blue light for antimicrobial properties, and red light for anti-inflammatory properties, may be selected. For example, the blue LED 231 emits a blue light in a wavelength range of between 380 nm to 500 nm, and the red LED 233 emits a red light in a wavelength between 600 nm to 700 nm. Other suitable wavelengths may be selected.

The hydrocolloid patch has both adhesion and therapeutic properties. The transparent adhesive hydrocolloid may include impregnated agents selected for having a complementary effect with the predetermined wavelength, for treatment of the afflicted region 262. The adhesive nature of the medication may be used to adhere the bottom window 221 directly to the afflicted region 262, or may be in the form of a patch 250.

Figure 15B:
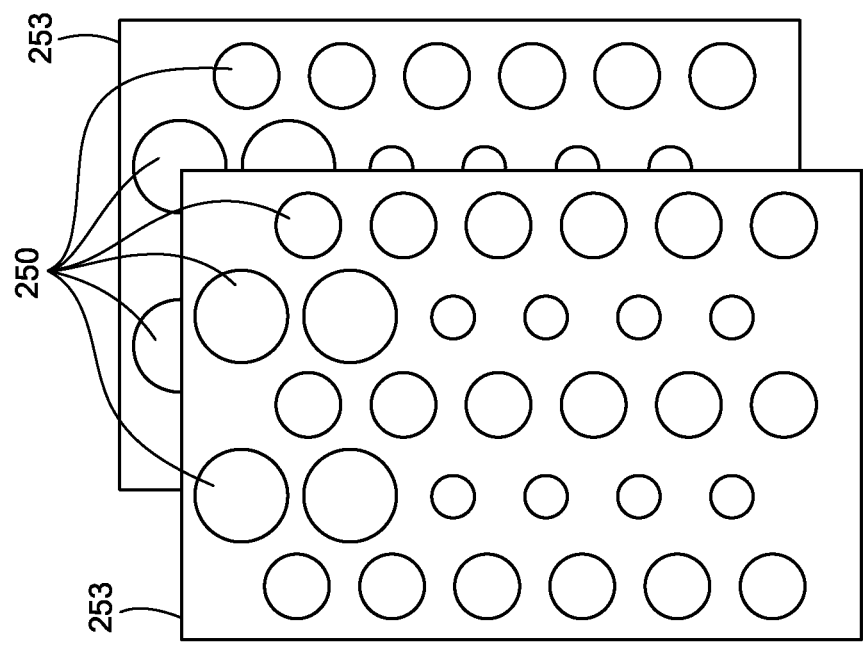
FIGS. 15A and 15B show deployment of the patch of FIG. 13.
Figure 15A:
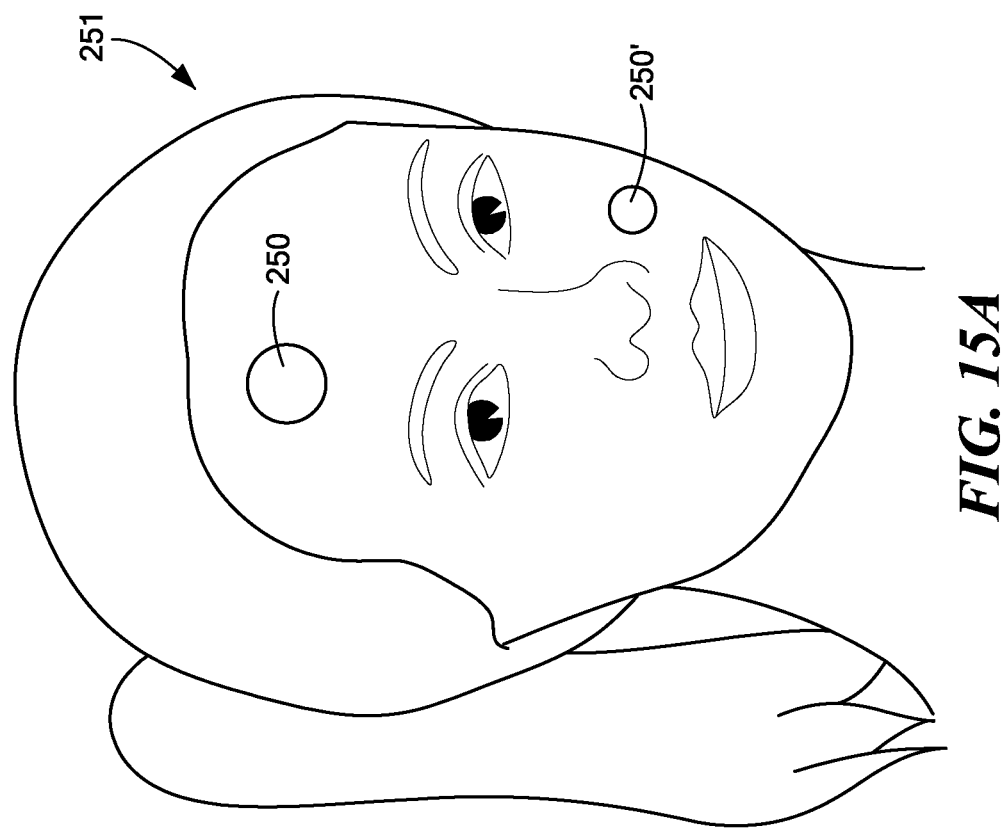

The hydrocolloid patch can absorb pus and fluid from the underlying acne lesion. The dermal device is adhered via the adhesive transparent hydrocolloid patch, such that the adhesive patch becomes disposed between the bottom window 221 and the afflicted dermal region 262 and has adhesive force for withstanding gravitational force exerted on the dermal device. Once the LED 231, 233 is activated, via the control logic, for invoking the light source according to a therapeutic sequence for directing light of a predetermined wavelength or wavelengths onto the afflicted dermal region. Any suitable agent impregnated in the hydrocolloid patch may be employed, however in a particular configuration 250 including at least one of acne-fighting salicylic acid and inflammation-reducing tea tree oil. FIGS. 15A and 15B show deployment of the patch 250 of FIG. 13. Referring to FIGS. 15A and 15B, transparent adhesive hydrocolloid patch 250 for adhering the device 200 to the patient dermal surface 260, and administering the phototherapy light while absorbing the pus and fluid and applying and directing the impregnated medication to the afflicted region 262.

The transparent adhesive hydrocolloid patch 250 can be impregnated with various agents and combination of agents for complementary purposes. The transparent nature enables transmission of the light therapy from the device 200, which is securely attached to the skin by the adhesive patch. The patch 250 is customizable in that it may be impregnated with various agents. For example, it may be impregnated with retinoids, benzoyl peroxide, clindamycin, salicylic acid, azelaic acid, erythromycin and any other suitable proprietary or brand formulations, particularly those having a synergistic beneficial combined effect with the red and blue light phototherapy.

FIG. 15A shows adhesion of the patch 250 to a patient 251, demonstrating alternate sized patches 250'. FIG. 15B shows fabrication of the patch 250 as a die-cut or similarly formed sheet 253 having an array of patches of various sizes. Therefore, the sheet 253 of patches 250 provides single use patches of various sizes for application in conjunction with the device 200, followed by prolonged wear of the patch 250 with the impregnated medication. In a particular configuration, the patch 250 is a pus- and fluid-absorbing hydrocolloid adhesive patch impregnated with acne fighting salicylic acid and inflammation reducing tea tree oil.

In an example usage scenario, the device 200 and patch 250 are applied to the afflicted region 262 for about 3 minutes, during which the device 200 is remains adhered while the timed light activated by the control 214 irradiates the afflicted area 262. The light unit may then be removed, and the patch remaining in place for continued therapeutic effect. However, any suitable usage cycle of light and patch administration may be performed.

Further indications for the adhesive phototherapy may include anti-aging, acne scars, psoriasis, dermatitis, vitiligo, alopecia, *pityriasis rosea*, parapsoriasis, cutaneous T-cell lymphoma, photo dermatoses, lichen planus, pruritus, *pityriasis* lichenoides, eczema, mycosis fungoides, polymorphic light eruption, cutaneous graft versus host disease, granuloma annulare, mastocytosis, chronic spontaneous urticaria, aesthetic and cosmetic concerns such as texture and tone focused treatments, and additional skin concerns. Various alterations to the phototherapy may be implemented, for example, and anti-aging regimen would likely entail only red light.

Treatment activation cycles of phototherapy may also be controlled by a mobile device application for activating and tracking treatment history and progress. In a particular configuration, the phototherapy device further comprises a network interface, and the control logic 245 transmits, via the network interface, activation information depicting timing, wavelength and duration of the activated phototherapy device. An app (application) on a smartphone conversant device receives the activation information for coalescing the activation information with a regimen of patient treatment data. Configurations above demonstrate therapeutic advantages of emitting a non-UV light, such as blue light in wavelengths from 380 nm to 500 nm. In particular, blue light in wavelengths of about 405 nm may be used. A module and adhesion for directing the therapeutic light to an acne lesion or other epidermal site symbiotically combines a topical hydrocolloid or similar substance with the light for epidermal treatment. FIGS. 16A-16D depict an alternate configuration including a deformable skirt or flange surrounding the light housing for facilitating placement and adherence. Referring to FIGS. 16A-16D, a self-adhered treatment device 300 includes a housing 310 and a flange defined by a deformable member 320 for skin contact and adhesion. In an example configuration, the deformable member 320 is formed from silicone, however other polymer and/or rubber based deformable mediums capable of resiliency and conforming to skin contour may be employed.

The device 300 is about 26 mm (1 inch) wide, having a generally round or rounded-square form factor. A thickness just under 1 cm (9 mm) provides a compact package suitable for epidermal adhesion for direct skin contact. A power switch contact 306 engages the light source driven by a power circuit, discussed below with respect to FIGS. 20A and 20B. Irradiated light 330 emanates from the bottom side 302 of the housing for direct irradiation onto the epidermal surface (skin).

Figure 16A:
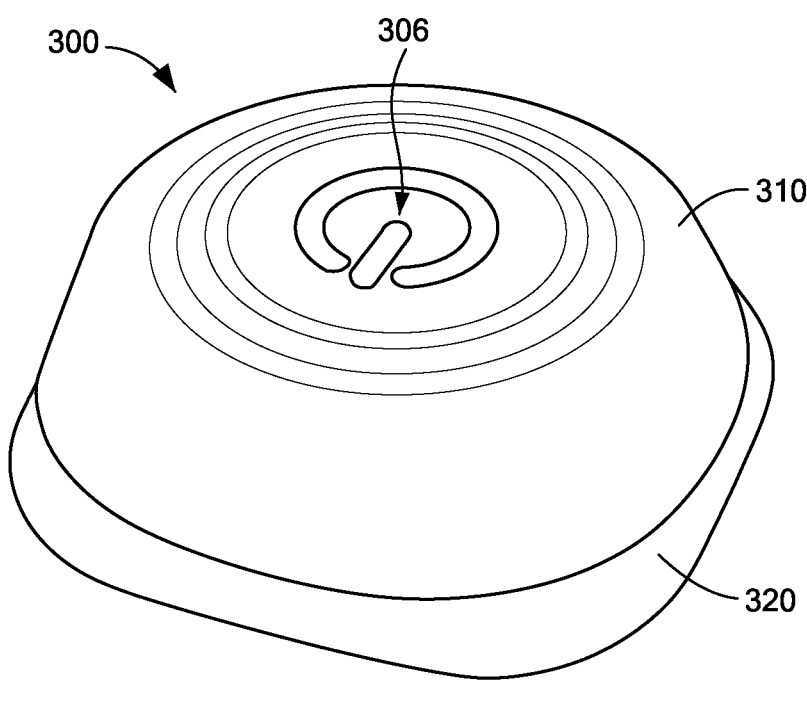
FIGS. 16A-16D depict an alternate configuration including a deformable flange surrounding the light housing for facilitating placement and adherence.
Figure 16B:
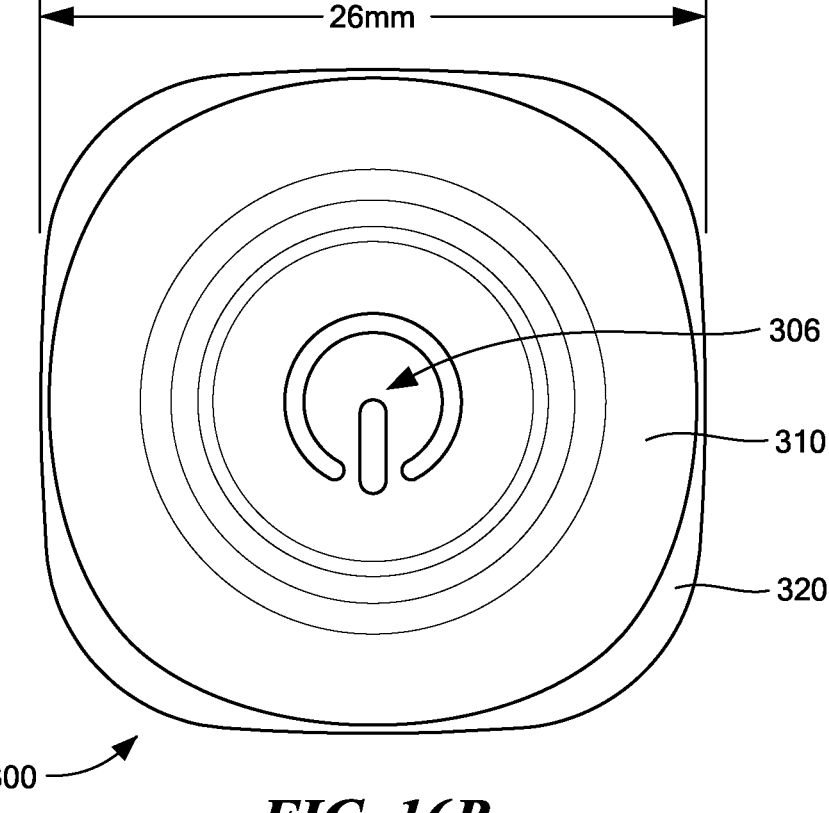
Figure 16C:
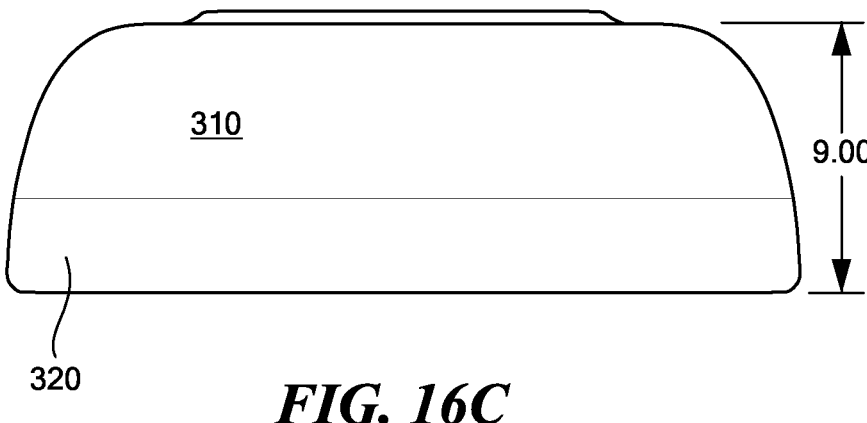
Figure 16D:
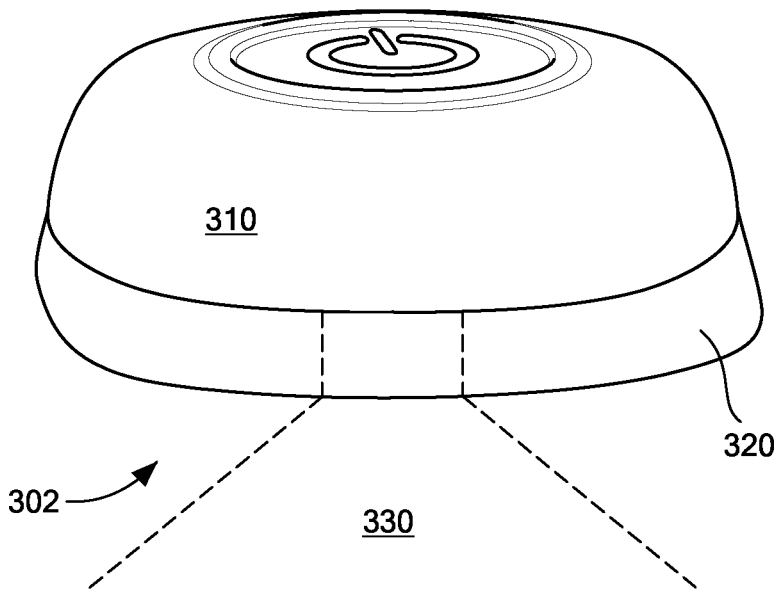
Figure 17:
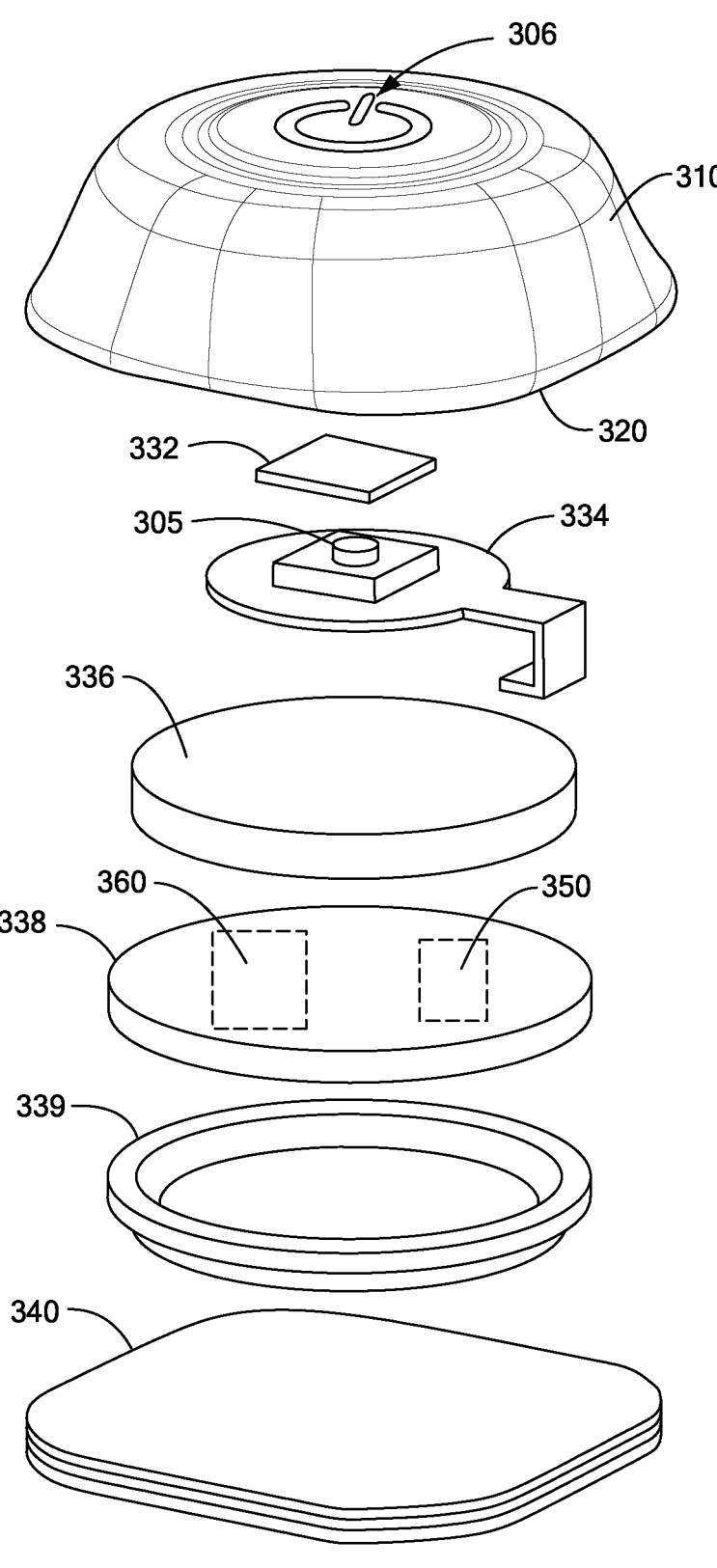
FIG. 17 shows an exploded view of the device of FIGS. 16A-16D.

FIG. 17 shows an exploded view of the device of FIGS. 16A-16D. Referring to FIGS. 16A-17, the site-mounted epidermal surface treatment device 300 includes a light source 350 configured for emission of therapeutic light 330 onto the epidermal surface. The housing 310 is adapted for placement on the epidermal surface such that the light source is contained within the housing 310. The switch 305 is disposed between a button board 334 and a spacer 332 for depression and actuation through the power switch contact 306. Depression and actuation of the switch 305 closes a circuit with a battery 336 for powering a circuit 360 on an LED board 338. The powered circuit 360 energizes one or more LEDs 350 of a suitable wavelength disposed on the underside of the LED board 338. A lens 339 passes the emitted light 330 for epidermal exposure. An engagement mechanism for locating and securing the housing 310 on the epidermal surface includes the deformable member 320 extending perimetrically around the housing 310. The deformable member is either layered with or adjacent to a patch 340, gel or cream for securing the housing 310.

The deformable member 320 forms a complete circumferential ring around the housing 310 for encapsulating the patch 340. Depending on construction, the deformable member 320 may extend completely over the housing and forms a continuous shroud, or may be attached to and extend from an edge of the housing 310. The power switch 305 is engaged via the power switch contact 306 on an upper side of the housing opposed from the epidermal surface. The power switch contact 306 may be continuous and/or integrated with a continuous shroud of the deformable member 320, or may be a separate depressable linkage for actuation. When the deformable member 320 extends completely over the housing and forms a continuous shroud, the power switch 305 is encapsulated under the continuous shroud such that the continuous shroud deforming for actuating travel of the power switch 305.

The adhesion is provided by the patch 340, cream or gel having transparent properties for passing the irradiated light 330. When a patch 340 is used, an adhesive on both sides adheres the housing and skirt to the epidermal surface. When a transparent gel or cream is used, the tackyness of the cream or gel serves to adhere. The skirt (deformable member 320) resiliently applies a surface contact bias to slightly compress the pad or crème to form a thin layer between the skin and the skirt for facilitating adhesion. When a patch is employed, it may have an area at least as large as an area defined by the circumference of the deformable member 320, to form a complete contact region encircling the treatment site where the pad is biased against the skin in a compressive arrangement with the skirt.

Figure 18:
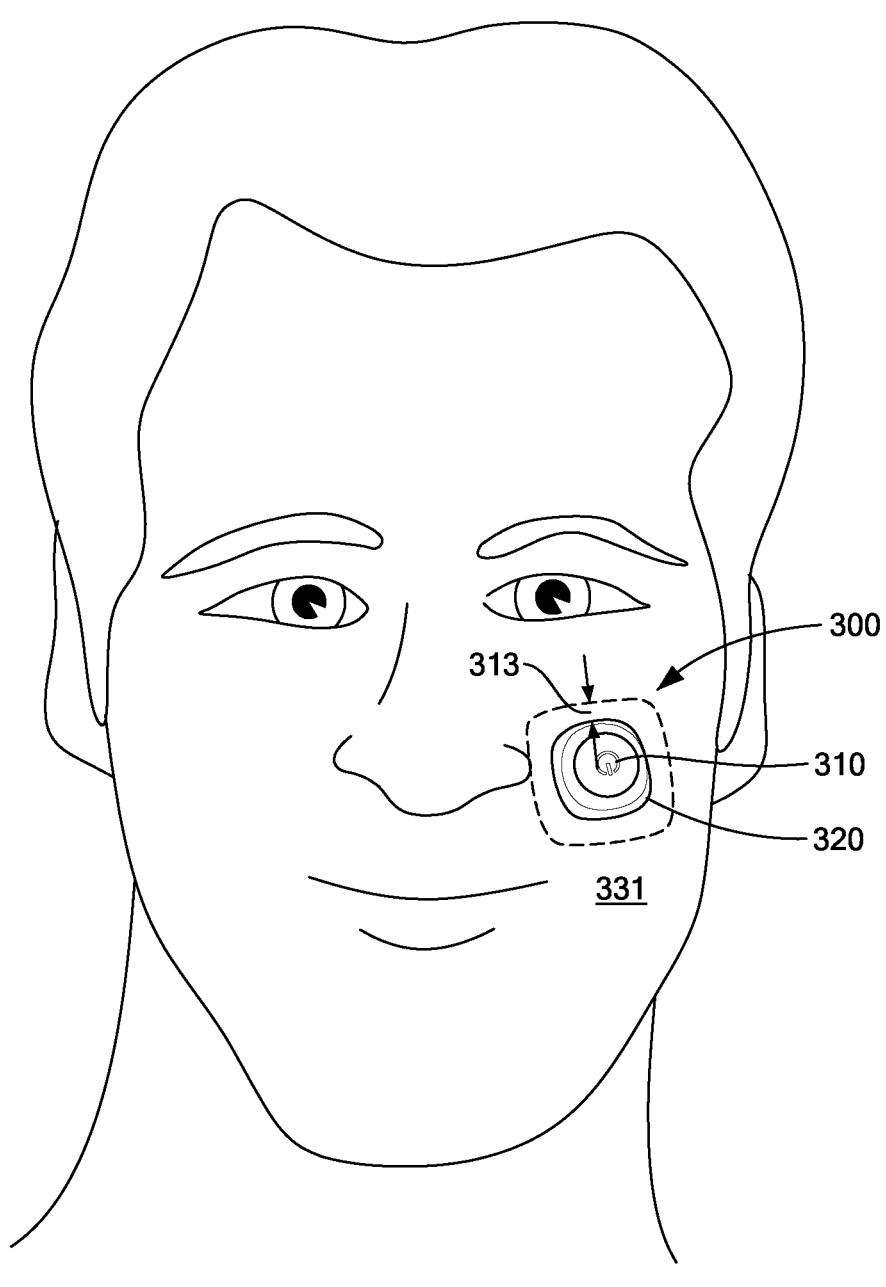
FIG. 18 shows the device of FIGS. 16A-17 deployed for facial acne treatment on an epidermal site of a patient.

FIG. 18 shows the device of FIGS. 16A-17 deployed for facial acne treatment on an epidermal site of a patient. Referring to FIGS. 16A-18, the device 300 is shown adhered to a treatment site on the epidermal surface 331 of a patient. The deformable member 320 is biased towards the epidermal surface 331 as it extends and covers/contacts a narrow strip 313 while the patch 340 and/or cream/gel forms a thin layer between the strip 313 and the epidermal surface 331.

Figure 19A:
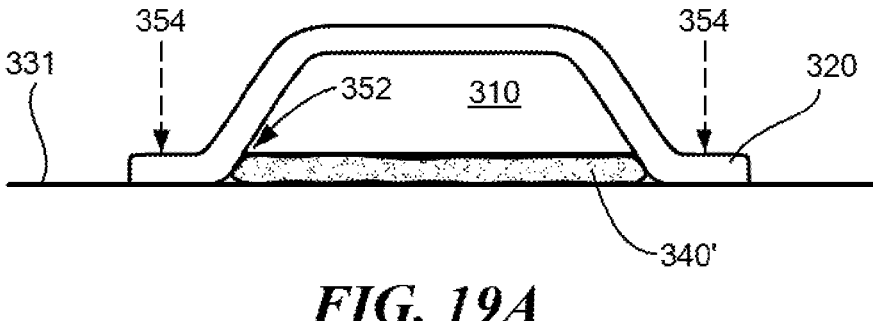
FIGS. 19A-19B show a side cutaway view of engagement of the deformable flange of FIGS. 16A-19B with the patient epidermal surface.
Figure 19B:
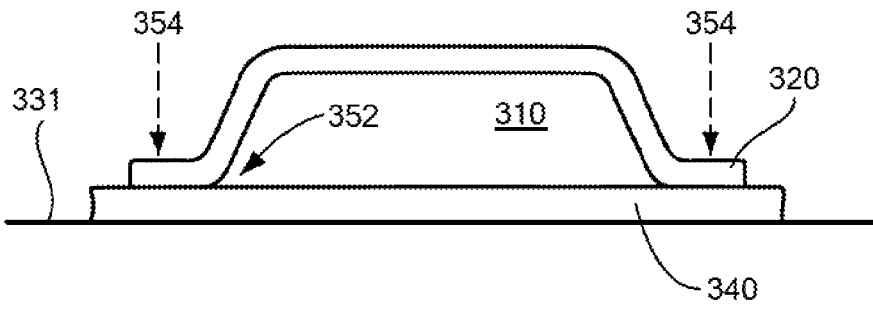

FIGS. 19A-19B show a side cutaway view of engagement of the deformable skirt of FIGS. 16A-19B with the patient epidermal surface 331. Referring to FIGS. 16A-19B, the deformable member 320 is oriented at a downward angle 352 toward the epidermal surface 331, such that the downward angle imposes a biasing force towards the epidermal surface, shown by arrows 334.

In FIG. 19A the engagement mechanism includes a transparent cream or gel 340,' typically a hydrocolloid, including medication for epidermal treatment. The cream 340' may be completely encapsulated between the housing 310 and the epidermal surface 331, as the deformable member 320 surrounds and contacts the epidermal surface. Alternatively, small amounts of the cream 340' may seep or form a compressed layer between the deformable member 320 and the epidermal surface 331. In FIG. 19B, the engagement mechanism includes a transparent patch 340, where the patch 340 is formed from a flexible planar material and has a shape based on a shape of the housing 310, so as to occupy the area beneath the housing and the deformable member 320.

The patch 340 is typically a hydrocolloid patch impregnated with a topical or therapeutic substance complementary to the therapeutic light. The patch is transparent and has an adhesive to contact and adhere the patch and the deformable member on a first side, and adhesive on a second side configured for contact with the epidermal surface. The patch 340 may be slightly larger than the area occupied by the deformable member, such that the deformable member 320 rests on and compresses the patch at a downward angle 352 from the biasing force of the patch 340. The patch 340 may be impregnated with a topical gel or cream, and collectively provides and adhesion in conjunction with the deformable member 320 upon contact with the epidermal surface 331.

Figure 20A:
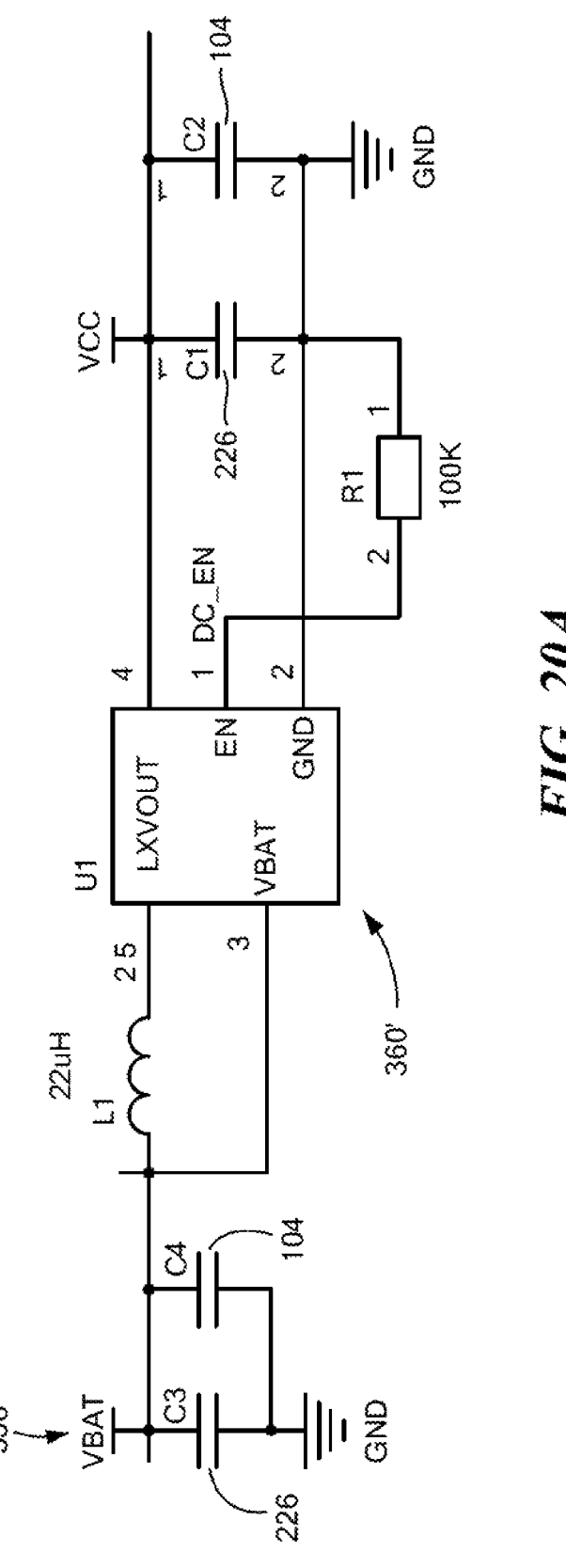
FIGS. 20A-20B show a circuit diagram of a circuit operable to energize the therapeutic light source in the housing of FIGS. 16A-19B.
Figure 20B:
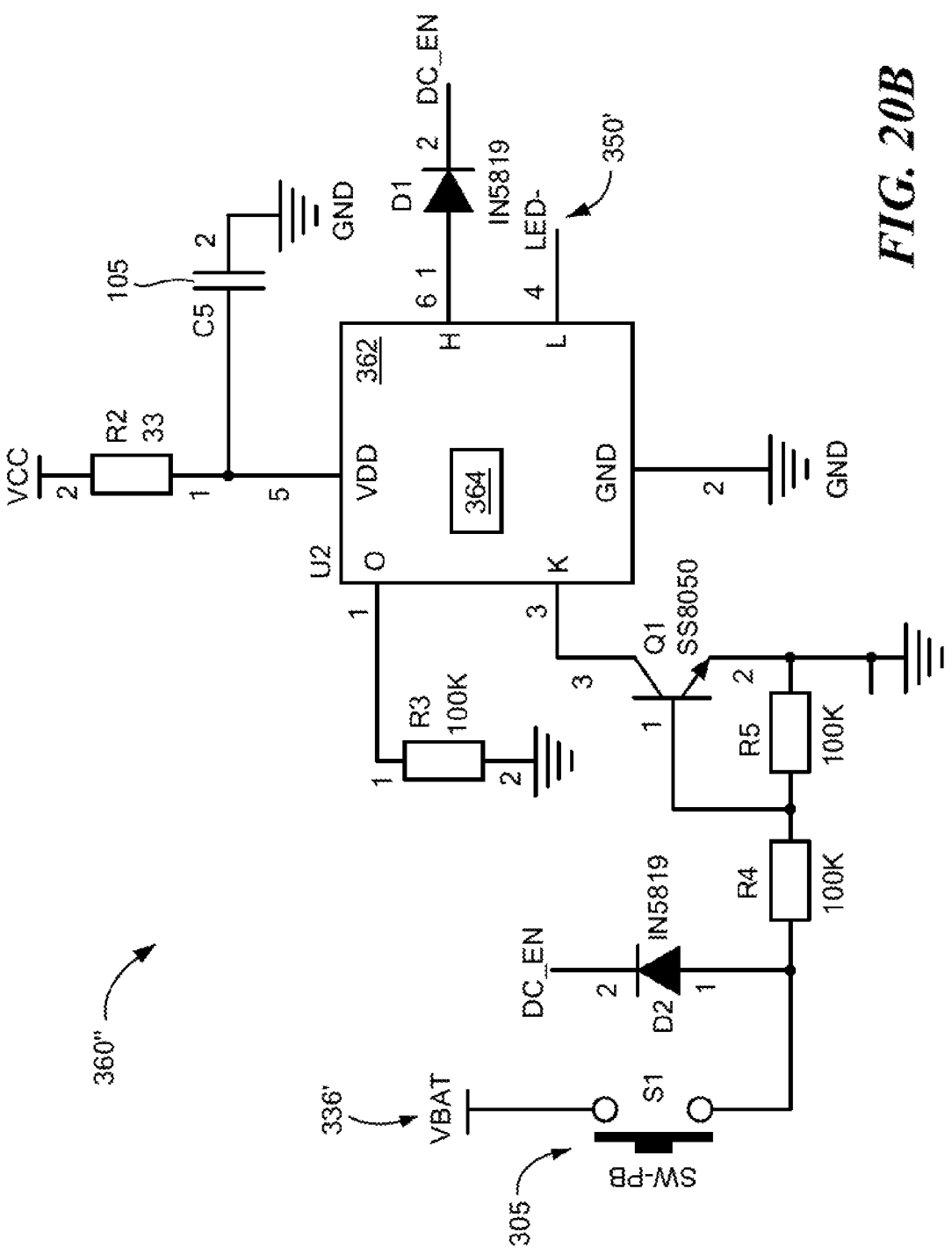

FIGS. 20A-20B show a circuit diagram of a circuit operable to energize the therapeutic light source in the housing of FIGS. 16A-19B. Referring to FIGS. 17, 20A and 20B, the LED board 338 further includes the power circuit 360. The power circuit connects to the light source 350 for energizing the therapeutic light for irradiation onto the epidermal surface 331, and is powered by the battery 336 connected between the switch 305 and the power circuit 360. The power circuit 360 includes circuits 360' and 360" responsive to the switch 305 for directing power to the light source and energizing the light source 350. The battery 336 connects to the positive VBAT terminal 336' for energizing the LED terminal 350'.

In the circuit 360", an IC (integrated circuit) chip 362 includes illumination logic 364 for activating the light source 350 according to a therapeutic pattern. The therapeutic pattern may include particular light intensities and wavelengths, and may regulate timing cycles of illumination to pulse the light over predetermined intervals. Although blue light is an expected regimen, LEDs of the light source 350 may be programmed with an intended wavelength/color of light emitted.

Figure 21A:
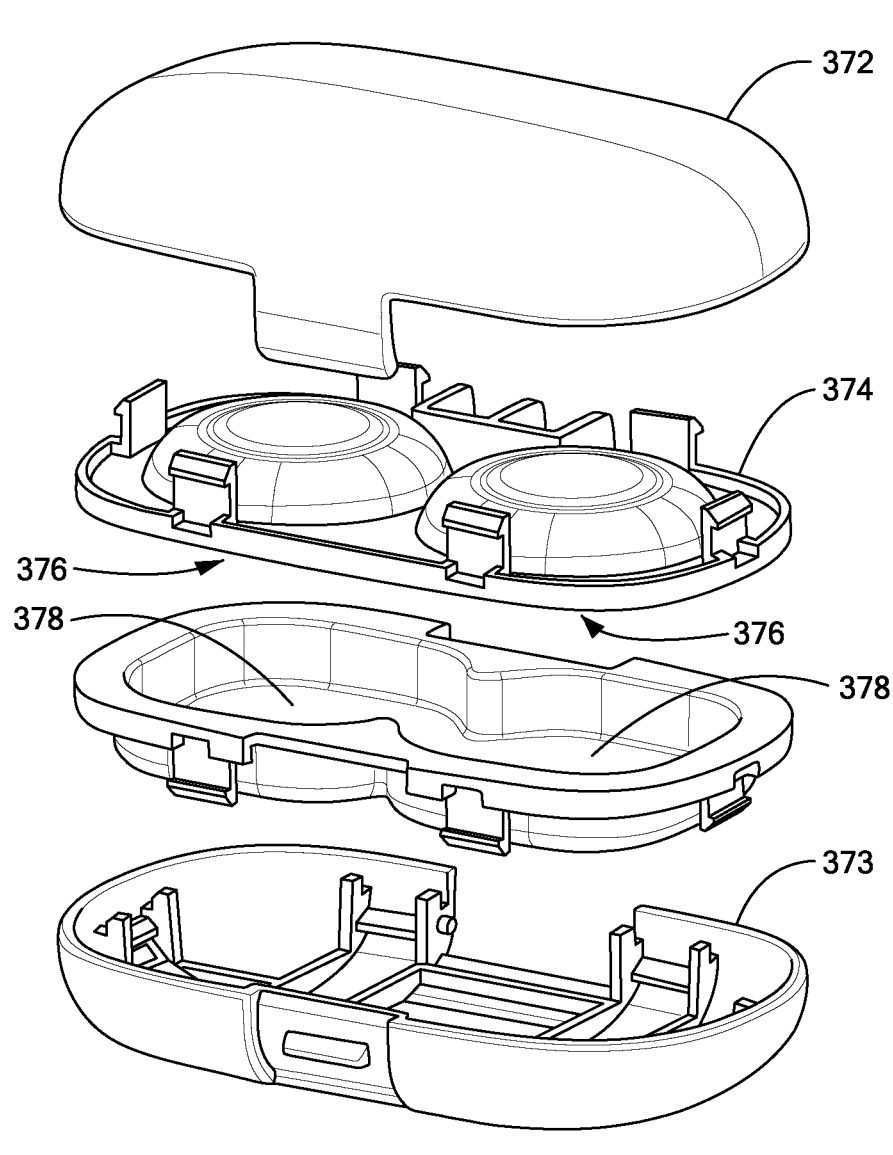
FIGS. 21A-21B show a packaging and storage encapsulation for the treatment device of FIGS. 16A-20B.
Figure 21B:
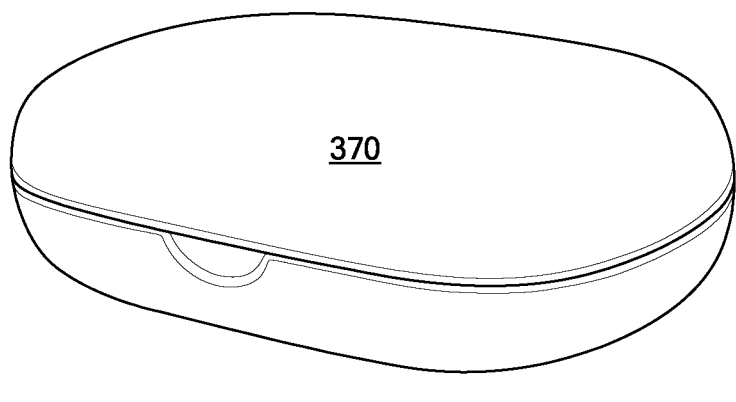

FIGS. 21A-21B show a packaging and storage encapsulation for the treatment device of FIGS. 16A-20B. Referring to FIGS. 16 and 21A-21B, as the device 300 is expected to be used iteratively, a plurality of devices may be employed over a treatment cycle. Further, each device 300 is targeted for a specific treatment site, defined by an acne breakout or occurrence ("pimple"). A portable enclosure 370 includes a top 372 enclosing an upper frame 374 having a plurality of receptacles 376, each with a corresponding base 378 and sized to fit inside a bottom 373. The upper frame 374/top 372 is hinged to the bottom 373 for closure.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed is:

1. A site-mounted epidermal surface treatment device, comprising:
   a light source configured for emission of therapeutic light onto an epidermal surface;
   a housing configured for facial adherence, the housing having a diameter adapted for placement and adhesion on the epidermal surface over a lesion, the light source contained within the housing;
   a deformable shroud extending over the housing, the housing having a width at least twice the height above the epidermal surface; and
   an engagement mechanism for securing the housing on the epidermal surface, the engagement mechanism including a deformable member extending perimetrically and outward around the housing,
   the deformable member flush and continuous with the deformable shroud for forming a complete circumferential ring around and extending beyond the housing and having a height of less than half the height of the housing,
   the deformable member oriented at a downward angle extending from the housing and tapering toward a flush engagement with the epidermal surface, the flush engagement responsive to a downward pressure perpendicular to the epidermal surface, and the downward angle imposing a biasing force towards the epidermal surface;,
   the deformable member capable of encapsulating a topical therapeutic agent between the flush engagement of the deformable member and the epidermal surface;
   the deformable member extending beyond the housing diameter to a circumference larger than the housing based on a width of the deformable member for defining an area for adhesion.

2. The device of claim 1, wherein the engagement mechanism includes a patch, the patch formed from a flexible planar material and having a shape based on a shape of the housing.

3. The device of claim 2, wherein the patch is hydrocolloid.

4. The device of claim 3, wherein the hydrocolloid patch is impregnatable with therapeutic agents.

5. The device of claim 3, wherein the patch has an area at least as large as an area defined by the circumference of the deformable member.

6. The device of claim 2, wherein the patch has an adhesive, the adhesive is in contact with the deformable member on a first side of the patch, and configured for contact with the epidermal surface on a second side of the patch.

7. The device of claim 1, wherein the continuous shroud extends completely over the housing.

8. The device of claim 7, wherein the deformable member is formed from silicone.

9. The device of claim 1, further comprising a power switch, the power switch on an upper side of the housing opposed from the epidermal surface.

10. The device of claim 9, wherein the power switch encapsulated under the continuous shroud, the continuous shroud deforming for actuating travel of the power switch.

11. The device of claim 9, further comprising
    a power circuit, the power circuit connected to the light source for energizing the therapeutic light for irradiation onto the epidermal surface; and

a battery connected between the switch and the power circuit, the power circuit responsive to the switch for directing power to the light source and energizing the light source.

12. The device of claim 1 wherein the deformable shroud and deformable member are defined by a continuous silicone surface.

13. A method for epidermal surface treatment comprising:

affixing a housing on a lesion on the epidermal surface using an engagement mechanism for securing the housing on the epidermal surface, the housing configured for facial adherence and having a diameter and adapted for placement and adhesion on the epidermal surface over the lesion, the housing having a width at least twice the height of the housing above the epidermal surface;

a deformable shroud extending over the housing;

engaging a deformable member extending perimetrically and outward around the housing with the epidermal surface, the deformable member flush and continuous with the deformable shroud for forming a complete circumferential ring around and extending beyond the housing and oriented at a downward angle extending from the housing and tapering toward a flush engagement with the epidermal surface, the flush engagement responsive to a downward pressure perpendicular to the epidermal surface, such that the downward angle imposes a biasing force towards the epidermal surface, the deformable member capable of encapsulating a topical therapeutic agent between the flush engagement of the deformable member and the epidermal surface;

the deformable member extending beyond the housing diameter to a circumference larger than the housing based on a width of the deformable member for defining an area for adhesion; and activating a light source contained within the housing to emit therapeutic light onto the epidermal surface.

14. The method of claim 13, further comprising:

applying an adhesive to a first and second side of a patch formed from a flexible, transparent planar material and having a shape based on a shape of the housing; and disposing the patch between the epidermal surface and the deformable member.

15. The method of claim 13, further comprising disposing the topical therapeutic agent between the deformable member and the epidermal surface.

* * * * *